(12) United States Patent
Ziv

(10) Patent No.: US 7,771,344 B2
(45) Date of Patent: Aug. 10, 2010

(54) DEVICE FOR THE PREVENTION OF URINARY INCONTINENCE IN FEMALES

(75) Inventor: Elan Ziv, Ramat Gan (IL)

(73) Assignee: ConTIPI Ltd., Caesarea (IL)

( * ) Notice: Subject to any disclaimer, the term of this patent is extended or adjusted under 35 U.S.C. 154(b) by 626 days.

(21) Appl. No.: 10/557,865

(22) PCT Filed: May 20, 2004

(86) PCT No.: PCT/IL2004/000433

§ 371 (c)(1),
(2), (4) Date: Oct. 23, 2006

(87) PCT Pub. No.: WO2004/103213

PCT Pub. Date: Dec. 2, 2004

(65) Prior Publication Data

US 2007/0203429 A1 Aug. 30, 2007

(30) Foreign Application Priority Data

May 22, 2003 (IL) .................................. 156070
Jul. 27, 2003 (IL) .................................. 157117

(51) Int. Cl.
*A61F 2/00* (2006.01)
(52) U.S. Cl. ........................................................ 600/29
(58) Field of Classification Search ............. 600/29–32; 128/DIG. 25
See application file for complete search history.

(56) References Cited

U.S. PATENT DOCUMENTS

| | | | |
|---|---|---|---|
| 4,212,301 A | 7/1980 | Johnson | |
| 4,726,805 A | 2/1988 | Sanders | |
| 4,823,814 A | 4/1989 | Drogendijk et al. | |
| 5,007,894 A | 4/1991 | Enhorning | |
| 5,224,494 A | 7/1993 | Enhorning | |
| 5,671,755 A | 9/1997 | Simon et al. | |
| 5,771,899 A | 6/1998 | Martelly et al. | |
| 5,894,842 A | 4/1999 | Rabin et al. | |
| 6,013,023 A | 1/2000 | Klingenstein | |
| 6,158,435 A | 12/2000 | Dorsey | |
| 6,189,535 B1 | 2/2001 | Enhorning | |
| 6,216,698 B1 | 4/2001 | Regula | |
| 6,415,484 B1 | 7/2002 | Moser | |
| 6,458,072 B1 | 10/2002 | Zunker | |

(Continued)

FOREIGN PATENT DOCUMENTS

EP 0955024 11/1999

(Continued)

OTHER PUBLICATIONS

Communication Relating to the Results of the Partial International Search Dated Aug. 18, 2009 From the International Searching Authority Re.: Application No. PCT/IL2009/000443.

(Continued)

*Primary Examiner*—John P Lacyk

(57) ABSTRACT

The invention concerns a device for minimizing involuntary urination in females adapted for being inserted into the vagina comprising both a pressure providing member and an anchoring member to prevent slippage of the device in the vagina. The invention further concerns a system comprising the device as well as an applicator for inserting the device to the vagina.

55 Claims, 36 Drawing Sheets

U.S. PATENT DOCUMENTS

| | | | |
|---|---|---|---|
| 6,478,726 | B1 | 11/2002 | Zunker |
| 6,503,190 | B1 | 1/2003 | Ulmsten et al. |
| 6,558,370 | B2 | 5/2003 | Moser |
| 6,676,594 | B1 | 1/2004 | Zunker et al. |
| 6,770,025 | B2 | 8/2004 | Zunker |
| 6,808,485 | B2 | 10/2004 | Zunker |
| 7,036,511 | B2 | 5/2006 | Nissenkorn |
| 2002/0138035 | A1 | 9/2002 | Hull, Jr. |
| 2003/0149334 | A1 | 8/2003 | Ulmsten et al. |
| 2003/0149392 | A1 | 8/2003 | Arnould |
| 2004/0122285 | A1 | 6/2004 | Zunker |
| 2004/0199100 | A1 | 10/2004 | LeMay et al. |
| 2007/0244352 | A1 | 10/2007 | Ziv |
| 2008/0149109 | A1 | 6/2008 | Ziv |
| 2008/0281149 | A1 | 11/2008 | Sinai et al. |

FOREIGN PATENT DOCUMENTS

| | | |
|---|---|---|
| FR | 2843700 | 2/2004 |
| GB | 1115727 | 5/1968 |
| GB | 2352181 | 1/2001 |
| JP | 06-133996 | 5/1994 |
| JP | 61-33996 | 5/1994 |
| WO | WO 96/01084 | 1/1996 |
| WO | WO 02/089704 | 11/2002 |
| WO | WO 03/047476 | 6/2003 |
| WO | WO 2004/103213 | 12/2004 |
| WO | WO 2005/087153 | 9/2005 |
| WO | WO 2005/087154 | 9/2005 |
| WO | WO 2006/097935 | 9/2006 |
| WO | WO 2008/010214 | 1/2008 |
| WO | WO 2008/079271 | 7/2008 |
| WO | WO 2008/152628 | 12/2008 |
| WO | WO 2009/044394 | 4/2009 |

OTHER PUBLICATIONS

Communication Under Rule 112 EPC Dated Oct. 22, 2007 From the European Patent Office Re.: Application No. 05718876.5.

European Search Report Under Rule 112 EPC Dated Dec. 27, 2007 From the European Patent Office Re.: Application No. 05718876.5.

International Preliminary Report on Patentability Dated Jul. 6, 2006 From the International Preliminary Examining Authority Re.: Application No. PCT/IL2005/000304.

International Search Report Dated Dec. 11, 2006 From the International Searching Authority Re.: Application No. PCT/IL06/00346.

International Search Report Dated Apr. 14, 2008 From the International Searching Authority Re.: Application No. PCT/IL2007/000893.

International Search Report Dated Sep. 23, 2005 From the International Searching Authority Re.: Application No. PCT/IL2005/000304.

Written Opinion Dated Dec. 11, 2006 From the International Searching Authority Re.: Application No. PCT/IL06/00346.

Written Opinion Dated Apr. 14, 2008 From the International Searching Authority Re.: Application No. PCT/IL2007/000893.

Written Opinion Dated Nov. 22, 2005 From the International Searching Authority Re.: Application No. PCT/IL2004/000433.

Written Opinion Dated Sep. 23, 2005 From the International Searching Authority Re.: Application No. PCT/IL2005/000304.

Communication Relating to the Results of the Partial International Search Dated Jan. 12, 2009 From the International Searching Authority Re.: Application No. PCT/IL2008/001292.

Notification Dated Dec. 17, 2008 From the Russian Patent Office Re.: Application No. 2006136791 and Its Translation Into English.

Office Action Dated Jan. 9, 2009 From the State Intellectual Property Office of the People's Republic of China Re.: Application No. 200580016245.2 and Its Translation Into English.

Communication Pursuant to Article 94(3) EPC Dated Apr. 16, 2009 From the European Patent Office Re.: Application No. 05718876.5.

Communication Relating to the Results of the International Search Dated Dec. 7, 2007 From the International Searching Authority Re.: Application No. PCT/IL2007/000893.

Communication Relating to the Results of the Partial International Search Dated Jan. 12, 2009 From the International Searching Authority Re.: Application No. PCT/IL2007/000893.

Communication Relating to the Results of the Partial International Search Dated Jan. 12, 2009 From the International Searching Authority Re.: Application No. PCT/IL2008/001292.

Communiction Pursuant to Article 94(3) EPC Dated Apr. 16, 2009 From the European Patent Office Re.: Application No. 05718877.3.

International Preliminary Report on Patentability Dated Oct. 14, 2008 From the International Preliminary Examining Authority Re.: Application No. PCT/IL06/00346.

International Preliminary Report on Patentability Dated Jul. 24, 2006 From the International Preliminary Examining Authority Re.: Application No. PCT/IL2005/000303.

International Preliminary Report on Patentability Dated Jan. 29, 2009 From the International Bureau of WIPO Re.: Application No. PCT/IL2007/000893.

International Search Report Dated Mar. 25, 2009 From the International Searching Authority Re.: Application No. PCT/IL2008/001292.

Notification Dated Dec. 17, 2008 From the Russian Patent Office Re.: Application No. 2006136791 and its Translation into English.

Office Action Date Sep. 1, 2008 From the Israeli Patent Office Re.: Application No. 157117.

Office Action Dated Jan. 9, 2009 From the State Intellectual Property Office of the People's Republic of China Re.: Application No. 200580016245.2 and Its Translation Into English.

Official Action Dated Apr. 17, 2009 From the Patent Office of the Russian Federation Re.: Application No. 2006136791 and Its Translation Into English.

Official Action Dated Dec. 17, 2008 From the Patent Office of the Russian Federation Re.: Application No. 2006136791.

Written Opinion Dated Mar. 25, 2009 From the International Searching Authority Re.: Application No. PCT/IL2008/001292.

Examiner's Report Dated Dec. 9, 2009 From the Australian Government, IP Australia Re.: Application No. 2005221424.

International Preliminary Report on Patentability Dated Dec. 23, 2009 From the International Bureau of WIPO Re.: Application No. PCT/IL2008/000786.

International Search Report and the Written Opinion Dated Oct. 28, 2009 From the International Searching Authority Re.: Application No. PCT/IL2009/000443.

Office Action Dated Jan. 18, 2010 From the Israel Patent Office Re.: Application No. 156070 and Its Translation Into English.

Official Action Dated Feb. 19, 2010 From the US Patent and Trademark Office Re.: U.S. Appl. No. 10/593,367.

Response Dated Feb. 22, 2010 to International Search Report and the Written Opinion of Oct. 28, 2009 From the International Searching Authority Re.: Application No. PCT/IL2009/000443.

Response Dated Dec. 27, 2009 to Official Action of Oct. 29, 2009 From the Federal Institute of Industrial and Intellectual Property, Patents and Trademarks, ROSPATENT, of the Russian Federation Re.: Application No. 2007138489.

Translation of Office Action Dated Jan. 19, 2010 From the State Intellectual Property Office of the People's Republic of China Re.: Application No. 200680017262.2.

International Preliminary Report on Patentability Dated Dec. 8, 2009 From the International Preliminary Examining Authority Re.: Application No. PCT/IL2008/001292.

International Search Report and the Written Opinion Dated Oct. 26, 2005 From the International Searching Authority Re.: Application No. PCT/IL2005/000303.

Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.

Written Opinion Dated May 23, 2006 From the International Preliminary Examining Authority Re.: Application No. PCT/IL2005/000303.

Communication Pursuant to Article 94(3) EPC Dated Apr. 16, 2009 From the European Patent Office Re.: Application No. 05718876.5.

Translation of Notification of Reasons of Rejection Dated Apr. 8, 2010 From the Japanese Patent Office Re.: Application No. 2007-503494.

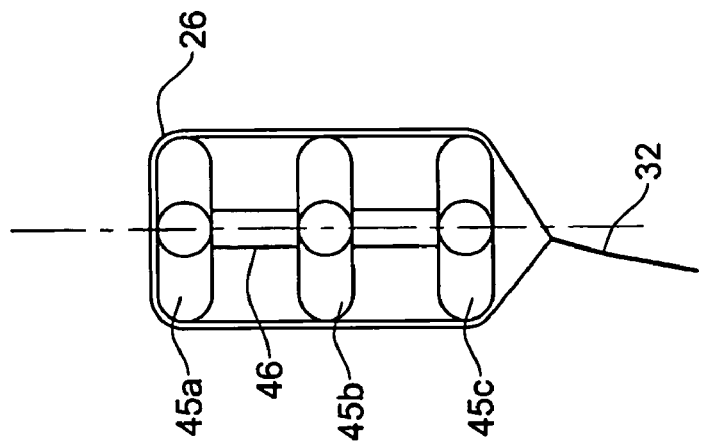
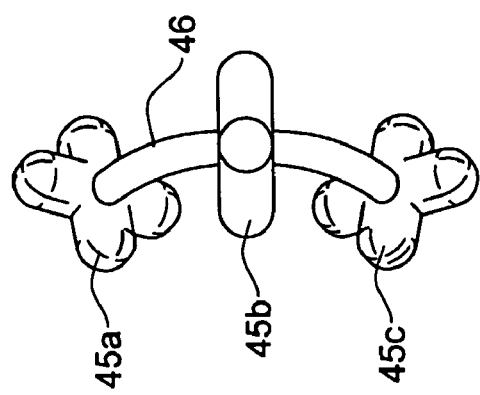
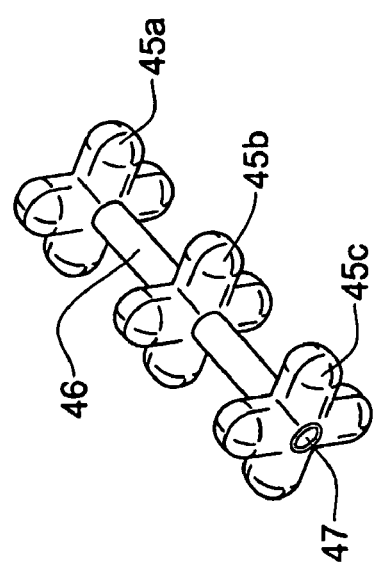

DEVICE FOR THE PREVENTION OF URINARY INCONTINENCE IN FEMALES

RELATED APPLICATIONS

The present application is a US National Phase of PCT/IL2004/000433, filed on May 20, 2004, which is related to Israeli application IL156070 filed on May 22, 2003 and Israeli application IL157117 filed on Jul. 27, 2003, the disclosures of which are incorporated herein by reference.

FIELD OF THE INVENTION

The present invention relates generally to the field of treatment for urinary incontinence in female patients.

BACKGROUND OF THE INVENTION

Urinary incontinence is a widespread problem among females. It is estimated that up to 50% of women occasionally leak urine involuntarily, and that approximately 25% of all women will seek medical advice at some point in order to deal with the problem. Stress incontinence, the most common type of urinary incontinence, refers to the involuntary loss of urine resulting from abdominal pressure rise, occurring during exercise, coughing, sneezing, laughing, etc. When stress incontinence occurs, it is usually the result of the abnormal descent of the urethra and bladder neck below the level of the pelvic floor. While many different factors may contribute to the development of stress incontinence, it is most prevalent among women who have had multiple vaginal deliveries. Stress incontinence is both aggravating and unpleasant for women, and it can also be embarrassing. Many women wear sanitary pads or diapers in order to deal with incontinence, though this is not a real solution to the problem and it can be very inconvenient and unreliable. In up to 18% of the cases, incontinence can be treated surgically. Surgical treatment may involve securing the paraurethral tissues to the periosteum of the pubic bone or the ileopectineal (Cooper's) ligament in order to elevate the bladder neck above the level of the pelvic floor and thereby distribute pressure equally to the bladder, the bladder neck, and the mid-urethra. Recently, a procedure known as "TVT" ("Tension Free Vaginal Tape") was developed, in which a mesh tape is implanted underneath mid-urethra, creating a hammock on which the urethra may "kink" during physical effort. However, surgery is only suitable for severe cases, and the majority of women experiencing incontinence do not need surgical solutions.

One modality of non-surgical treatment involves the use of devices that are inserted into the vagina, either by a medical practitioner or by the woman herself. Most devices are designed to apply pressure against the bladder neck so as to inhibit or completely block the flow of urine through the urethra. A variety of such devices are known in the art. For example, refer to U.S. Pat. No. 5,618,256 to Reimer, entitled, "Device for Arrangement in the Vagina for Prevention of Involuntary Urination with Females and an Applicator for use in Insertion of the Device;" U.S. Pat. No. 5,785,640 to Kresch, entitled "Method for Treating Female Incontinence;" U.S. Pat. No. 4,920,986 to Biswas, entitled, "Urinary Incontinence Device;" U.S. Pat. No. 5,417,226 to Juma, entitled, "Female Anti-Incontinence Device;" U.S. Pat. No. 5,386,836 to Biswas, entitled, "Urinary Incontinence Device;" and U.S. Pat. No. 5,007,894 to Enhorning, entitled, "Female Incontinence Device."

A number of devices are constructed so as to completely block the urethra and thus they need to be removed or collapsed in order to allow the woman to urinate. Another type of vaginal devices have specialized shapes that do not completely block the bladder neck thus allowing voluntary urination while decreasing involuntary urination. However, these devices tend to be large, uncomfortable, and intrusive. They also tend to cause irritation or soreness to the vagina. Moreover, such devices are expensive to manufacture, and therefore, they are designed to be re-usable and/or to remain in the vagina for an extended period of time. Such devices are normally made from large bodies of resilient material, such as plastic or hard rubber, in order to preserve their functioning for the required amount of time. Most devices known in the art also tend to be difficult or painful to insert and/or remove. In order to correctly inhibit urine flow, the device needs to be properly positioned in the vaginal canal in a specific orientation. As stated previously, a doctor may be required to properly position the device. Especially in cases where a doctor has to insert the device, the device is adapted for remaining in the vagina for a prolonged period of time. When positioned in the vagina for an extended period of the time, the device may cause vaginal infections, necrosis, or bleeding. Furthermore, the device may block or inhibit the flow of normal body secretions through the vagina, and may cause a foul-smelling discharge. In cases where the device is designed to be inserted by the woman herself, the device often has to be removed, cleaned, and then re-inserted after a predetermined number of hours.

Another problem encountered by state of the art devices resides in their tendency to slip backwards toward the uterine cervix, so that the pressure on the urethra which should have been applied by providing pressure through the proximal third of the vagina is misplaced.

No disposable vaginal device for controlling urinary incontinence has been successfully marketed and used by women. There is a need for a device for controlling involuntary urination that is easy and comfortable for a woman to use, that works effectively and reliably, and that is completely sanitary and hygienic, and preferably disposable. There is further need for a device that is anchored properly in the vagina and does not slip backwards so that the pressure underneath the urethra is maintained correctly.

SUMMARY OF THE INVENTION

It is therefore a main goal of the present invention to provide a novel device for the treatment of urinary incontinence in females. The device of the present invention is adapted to be disposable, worn only for a maximum of 6-8 hours and then discarded, and replaced with a new device (if needed). The device of the present invention is simple and easy to use, and is inserted effortlessly in the same user-friendly and familiar manner that a tampon is inserted into the vagina during menstruation. As opposed to large and intrusive devices of the prior art, the device of the present invention is comfortable, and, once inserted, the woman need not think about it again until it is removed. Other features and advantages of the present invention will become more readily apparent from the summary and description that follow.

When involuntary urination occurs during physical effort or stress, it is usually the result of the abnormal descent of the bladder neck and the urethra into a low position, away from the intra-abdominal pressure system. This "hyper mobility" is the result of some injury to the support mechanism which normally keeps the urethra and the bladder neck in a raised position, along the backside of the pubic bone. The lowering of the bladder neck and the urethra that occur, for example, when a woman coughs, sneezes, or laughs, causing involuntary leakage of urine. The device of the present invention is designed so as to provide a "cradle" or shelf-like support to the urethra whenever the urethra descends momentarily, so as to minimize or prevent the leakage of urine. By one embodiment of the invention the device does not apply direct pressure against the urethra or the bladder neck, but only provides support when there is a rise in abdominal pressure. By this embodiment voluntary urination is possible while involuntary urination is eliminated or minimized. By another embodiment, suitable for woman undergoing physical exercise the device applies direct pressure on the urethra thus possibly completely blocking the passage of urine (both voluntary and involuntary) there through. This device might have to be removed prior to urination.

It will be appreciated that the device of the present invention is suitable for mild to moderate cases of urinary incontinence, where a woman's daily routine and general quality of life are disturbed by the involuntary leakage of urine occurring every so often, though not to such an extent as to require surgical intervention. A woman may chose to wear the device, for example, only when she plans on doing exercise or going out of the house. It is appreciated that the device of the present invention allows a women to have control over her incontinence. She can use the device whenever she desires, and no doctor is needed to insert or remove the device. Also, the device is safe and sanitary, so that wearing it will not lead to infections or other harmful conditions. Additionally no one else will know that she is wearing it, and, because it is comfortable to wear, she herself will hardly notice the presence of the device while it is being worn. In essence, the device accomplishes the same goal that surgery accomplishes: it provides support for the mid-urethra so as to prevent unwanted leakage of urine but without the distress of going through a surgical procedure.

The device of the present invention is manufactured to be inserted through means of applicator, which may be identical or similar to a menstrual tampon applicator, or by a specially designed applicator. Thus, the woman does not need to touch herself in order to properly insert the device. Removal of the device is also accomplished easily, preferably through the use of a string.

The present invention relates to a disposable device for preventing involuntary urination in females adapted for being inserted into the vagina, comprising:

(a) an internal support structure comprising:

(i) a pressure providing member capable of transition between a first collapsed position and a second expanded position, adapted for providing pressure, through the vaginal wall, on the mid-urethral region following insertion of the device into the vagina;

(ii) an anchoring member, said anchoring member adapted for anchoring the internal support structure following insertion of the device into the vagina, so as to prevent movement of the device into the apex of the vagina; the pressure providing member and the anchoring member being spaced apart;

(b) pulling means for removal the device from the vagina, so that when said pressure providing member and said support member are in the collapsed position the internal device may be inserted or removed from the vagina and when said pressure providing member and said anchoring member are in the second expanded position, the device is positioned in the vagina in such a manner so as to provide pressure through the vaginal wall on the mid urethra, minimizing involuntary urination.

The anchoring member can be rigid or flexible. Preferably the anchoring member is capable of transition between a first collapsed position and a second expanded position. Preferably the internal support structure is enclosed within a cover for covering said internal support structure made of a flexible material.

The two members may be integral, constituting a single construction, and the spacing is achieved by placing them at a distance from each other is a part of said construction. Where the two members are separate the spacing is achieved by a special spacer, which is preferably flexible.

The device of the invention is composed of a functional unit being termed the internal support structure. The structure is composed of two member connected to each other in a spaced manner either by the construction or by an element termed "spacer". The spacer is usually composed of a flexible rod, spacing the two members from each other in the longitude axis. Although in some drawing the two members are separate constructions, in some embodiments of the inventions the two members are a single integrated element, have both the function of anchoring and pressure provision and the spacer is a part of the single construction separation spatially the two functions.

One member termed "pressure providing member" is used to apply either direct or indirect pressure on the mid urethra to decrease involuntary urination. The other member "anchoring member" is merely used to prevent backward slippage of the device to the apex of the vagina so that the device is positioned properly in the vagina even during physical exercise.

Both members can be in two positions—a collapsed position which enables their insertion and removal from the vagina and an expanded position enabling the application of pressure or anchoring inside the vagina.

Typically the two members have the same construction and the same mechanism for transition from the collapsed to the expanded positions but this is not necessarily so and the anchoring member may have a different structure or mechanism as compared to the pressure applying member, or may be completely rigid.

Typically the collapsed position is achieved either through the inner walls of an applicator for insertion into the vagina, or through the pulling of the removal means (such as a string) for removing the device from the vagina. The expanded position is assumed once the device is pulled out of the vagina.

The invention also concerns a system for inserting a disposable device for preventing involuntary urination in females into the vagina comprising: a device of the invention; and an applicator coupled to said device for facilitating insertion of the device into the vagina.

By one embodiment of the invention the device of the present invention is not designed to put direct pressure against the urethra. Rather, the device according to one embodiment is designed to provide a cradle-like support for the mid-urethra when the urethra descends abnormally below the level of the pelvic floor as the result of an increase in intra-abdominal pressure.

In accordance with this embodiment, which will be termed hereinafter "the non direct mid urethra pressure embodiment" the device of the invention is inserted into the vagina, is changed from a first, collapsed position to a second, expanded position wherein specialized parts of the pressure providing member are distanced from its main central axis so as to apply outward pressure on the vaginal wall and through this on the mid urethra. The increased support of the mid urethra is such that voluntary urination is still possible, while involuntary urination is decreased or completely eliminated. This allows the woman wearing the device in accordance with this embodiment of the invention, to keep the device for prolonged periods of time, urinating at will when the device is inserted, while decreasing her involuntary urination. However, at times especially during heavy physical exercise, (such as aerobic exercises), indirect pressure to the mid urethra may not suffice to eliminate the involuntary urination, and there would be need for direct pressure.

In accordance with a second embodiment of the device, termed "direct pressure on mid urethra embodiment" the device of the invention again is positioned in the vagina and is changed from a first collapsed position, to a second expanded position, wherein specific parts of the pressure providing member are distanced from its central axis, however, at least one part of the device, in the second expanded position, provides direct pressure against the mid urethra, thus essentially decreasing, or eliminating all urination both voluntary and involuntary. Such a device is worn by the woman prior to physical exercise, and is removed when the woman wishes to urinate.

The internal support structure may function through any suitable means known in the art. In certain preferred embodiments, the two members of the internal support structure have an inactive collapsed configuration when it is inside of the applicator, prior to insertion into the vagina, and an active, expanded configuration that is adopted following insertion into the vagina. In the inactive configuration, the two members of the support structure are in a compact form, inside of the applicator. Once inserted in to the vagina, the pressure providing member assumes an active open configuration, in which indirect support of the urethra in accordance with the first embodiment or direct pressure in accordance with the second embodiment is provided. In some examples, movement to the active configuration corresponds to an expansion in the size of the two members of the support structure. In other examples, the shape or form of the support structure is changed following insertion into the vagina, so as to provide the appropriate level of support to the vaginal wall (these examples will be described further).

While some of the prior art devices have also a configuration transitional between a collapsed and an expanded position, most of them suffer from the drawback that the device can relatively freely move backwards in the vagina, so that the expansion which should put maximal pressure at mid vagina, so as to provide pressure for the mid urethra, may be misplaced due to slippage of the device.

The device of the present invention overcomes this problem by means of at least one anchoring member present when the device is in the vagina, posterior (towards the uterine cervix) to the pressure providing member, which essentially prevents the slippage of the device upwards towards the cervix. Preferably, the device of the invention has two anchoring members, positioned at the end of the device pointing towards the cervix, but in some embodiments one such member is sufficient to eliminate displacement (slippage). Each anchoring member is capable of transitioning between a compact first position wherein the device is inserted or removed from the vagina, and an expanded position, wherein the anchors are expanded so that the cross section of the device is increased. As indicated above the anchoring members may be identical or different from the pressure providing members.

According to some embodiments of the present invention, the internal support structure functions through pneumatic means. In one embodiment, the internal support structure comprises at least one balloon adapted for being inflated upon insertion of the device into the vagina. The balloon may be adapted for being filled with air (or any other suitable gas) or any appropriate liquid medium as well. The balloon is positioned inside of the applicator in a collapsed configuration prior to insertion. When the balloon is advanced, by means of an active plunger, through the end of the applicator and into the vagina, the balloon becomes such that it expands to a predetermined size inside of the vagina. A one-way flexible valve mechanism prevents the escape of air following inflation of the balloon. To remove the device, a string that is coupled to the valve mechanism is pulled. This results in deflation of the balloon, and thus allows for the removal of the device from the vagina. In this embodiment a single construction being the balloon serves both as the pressure providing member and as the anchoring member as well as the spacer between the two. In some embodiments, the internal support structure comprises three balloons that are adapted for assuming inflated positions at different locations along the length of the vagina. The balloons are preferably formed from any suitable semi-expanded material such as polyurethane or silicone. The first balloon, serving as the pressure providing member, is located so as to provide support under the mid-urethra, and preferably has a substantially circular shape. The second balloon, which serves as an anchoring member, is located so as to anchor or secure the device within a place of lower wall tension in the vagina. Preferably, the second balloon is also substantially circular, and has a diameter greater than the first balloon. The first and second balloons are designed to expand outward, towards the anterior and posterior walls of the vagina. The third balloon, which also serves as an anchoring member, is located at the end of the support structure (assuming a position at the internal-most region of the vagina), and serves to prevent backward movement of the device. The third balloon expands in a longitudinal, cylindrical manner. It is to be appreciated that preferred embodiments of the present invention may comprise between 1-3 balloons, of suitable sizes, designed for achieving the aforementioned goals. In some examples, one or more of the balloons have at least one opening extending therethrough for allowing the passage of bodily fluids and secretions through the vagina.

It is to be emphasized that in the preferred embodiments of the present invention the device includes a cover surrounding the internal support structure, which is inserted into the vagina along with the internal support structure. The cover is formed from a flexible material such as viscose, woven cloth, nylon or lycra, that allows said cover to change shape or size in accordance with the internal support structure. The internal support structure, together with the cover, forms the cradle for the mid-urethra section to prevent involuntary leakage of urine.

According to other embodiments of the present invention, the internal support structure functions through mechanical means. In certain preferred embodiments, the internal support structure comprises at least one expanded support arc (for supporting the vaginal wall), and a plurality of support arms coupled to said arc for facilitating widening of the support arc following insertion of the device into the vagina. If a single arc is used the arc serves both as the pressure providing member and as the anchoring member. The support arc may be designed so as to face the front or the back of the vagina. When the support structure adopts an active-expanded configuration, the support arc becomes widened, and anchored to the vaginal walls, thus forming the cradle for the mid-urethra in conjunction with the cover. It is to be appreciated that a variety of mechanically-operated internal structures could be conceived, for assuming an active configuration inside of the vagina, and for providing a cradle-like support for the urethra in combination with the device cover.

According to further embodiments of the present invention, the internal support structure functions through pneumo-mechanical means. In one preferred embodiment, the internal support structure comprises at least one balloon coupled to at least two support members and constructed such that when the balloon is inflated upon insertion of the device into the vagina, the support members extend and press against the cover such that said cover forms a cradle for the mid-urethra. In this embodiment the balloon serves both as the pressure providing member and as the anchoring member. In another preferred embodiment, the internal support structure comprises a first balloon, a second balloon, and a third balloon, wherein each balloon is coupled to two support members. The first balloon and support members function constitute the pressure providing member, to provide mid-urethral support and to create a cradle for the mid-urethra in combination with the cover of the device. The second balloon and corresponding support members constitute the anchoring member serve to anchor the device into place in the vaginal canal. The third balloon and corresponding support member serves to prevent backward movement of the device in the vagina as a possible additional anchoring member. It is appreciated that the length, flexibility, and curvature of the support members is determined according to the function of the respective support members and the particular location in the vagina which it is to adopt. In the aforementioned examples, the balloons may be inflated through any suitable means known in the art. Preferably, the balloon(s) becomes inflated through pushing on an active plunger following insertion of the device into the vagina. A one-way flexible valve prevents escape of air after its inflation. Removal of the device is preferably accomplished through a string that is coupled to said valve. Pulling on the string causes deflation of the balloon(s), and subsequent collapsing of the support members such that the device can be withdrawn with ease from the vagina.

According to other embodiments of the present invention, the internal support structure comprises an elongated body and at least one semi-flexible star-shaped member positioned on said elongated body which serves as the "spacer. In one preferred embodiment, the elongated body, spacer, is formed from a flexible material so as to easily fit the contours of the vagina. Preferably, there are three star-shaped members, though any number of stars is possible, preferably between one and three. The star-shaped members are attached to the elongated body so as to extend, in a substantially perpendicular manner, from the longitudinal axis of the elongated body. In certain preferred embodiments, the star-shaped members are formed from hard material such as polycarbonate, or alternatively from flexible material such as polyethylene, polyurethane, silicone, or any other suitable material, and each star-shaped member has four prongs. When inserted into the vagina, the urethral cradle is formed by the cover of the device, tented by the prongs of the star-shaped members. For removal, a string that is coupled to the cover is pulled, causing said cover to straighten and weaken the tenting effect, enabling removal of the device from inside the vagina. In some embodiments, the prongs of the star-shaped members are compressed inside of the applicator prior to the insertion of the device. Once inserted, the star-shaped members assume an active configuration (with the prongs extending towards the vaginal walls). According to preferred embodiments of the present invention, at least one prong of the star-shaped member comprises an inflatable balloon positioned at the end thereof, for anchoring the respective star into place. Preferably, each of the four prongs of each star-shaped member comprises one inflatable balloon positioned at the end thereof.

According to further preferred embodiments of the present invention, the internal support structure comprises a star-shaped member coupled to the ends of four extending arms. The star-shaped member serves to provide mid-urethral support (in conjunction with the cover). In one preferred embodiment, the extending arms are made of an elastic material. While inside of the applicator, the extending arms are compressed towards one another. Once released from the applicator, they move away from one another, applying gentle pressure on the vaginal walls and stabilizing the positioning of the device. By another embodiment the extending arms extend through a telescopic mechanism, for example, activated by a coil. By another embodiment the extending arm extends through the mechanism of the screw as will be explained hereinbellow. It will be appreciated that this preferred embodiment also provides a means for the treatment of pelvic organ prolapse. In certain preferred embodiments, the star-shaped member comprises four openings (one in each prong), which the extending arms pass through and then move away from one another when the device is being inserted into the vagina.

BRIEF DESCRIPTION OF THE DRAWINGS

The present invention will now be described, by way of example only, with reference to the accompanying drawings, wherein:

FIG. 3a is a schematic side view of the device in an inactive, closed configuration, prior to insertion into the vagina. FIGS. 3b, 3c, and 3d are cross sections of the device of FIG. 3a, taken through lines A-A and B-B. FIG. 3e is a schematic side view of the device in an active, open configuration, following insertion into the vagina.

FIG. 4a shows the device in an inactive, closed configuration. FIG. 4b shows the device in an active, open configuration.

FIGS. 5a-5d and FIGS. 6a-6c illustrate another preferred embodiment of the device of the present invention. FIGS. 5a and 5b show isometric views of two possibilities for the internal support structure of the device. FIG. 5c shows the internal support structure of the device positioned inside of a cover. FIG. 5d is a side view of one star-shaped member of the device, illustrating the manner in which the star-shaped member and the cover provide support for the urethra. FIG. 6a is a cross-sectional view of the device housed inside of an applicator. FIG. 6b is a side view of the device/applicator of FIG. 6a, showing how the device is pushed out from the applicator. FIG. 6c is an isometric view of the device housed inside a second type of applicator, said applicator being specially designed for use with this preferred embodiment.

FIGS. 7a-7d show various views of a star-shaped member of the device. FIG. 7a is an isometric view of the star-shaped member. FIGS. 7b and 7c show side views of the star-shaped member. FIG. 7d shows a top view of the star-shaped member as it appears inside the vagina. FIG. 8 illustrates a side view of the device housed inside of an applicator, as said device is being pushed out from the applicator during its insertion.

FIG. 9a is a schematic side view of the device as it appears inside of an applicator. FIG. 9b is a cross-sectional side view of the device following insertion into the body. FIG. 9c is a cross-sectional view through one of the star-shaped members of the device.

FIG. 10a is a cross-sectional side view of the device inside of an applicator. FIG. 10b is a cross-sectional side view of the device after it has been released from the applicator and positioned inside of the vagina. FIG. 10c is an isometric view, taken from the exterior, of the device positioned inside of the vagina.

FIG. 11a illustrates a schematic side view of the device in the collapsed position (inside the applicator) and FIG. 11b illustrates the device in the expanded position; FIGS. 11c and 11d illustrate a cross section of pressure providing member (101) in the collapsed and expanded position respectively; and FIGS. 11e and 11f illustrate an isometric view of the pressure providing member (101) in the collapsed and expanded position, respectively.

DETAILED DESCRIPTION OF THE INVENTION

It is appreciated that the preferred embodiments herein provided are meant only to illustrate certain preferred embodiments of the present invention. They are in no way intended to limit the scope of the invention, as set out in the claims. For example, it will be appreciated that the non-surgical device of the present invention could operate through a multitude of different means, all for accomplishing the same function of providing support for the mid-urethra, while not applying any pressure. This is accomplished through the use of an internal structure and cover that, together, form a cradle-like support for the urethra to produce a kinking effect whenever there is an abdominal pressure rise that would otherwise result in the unwanted leakage of urine.

Figure 1:
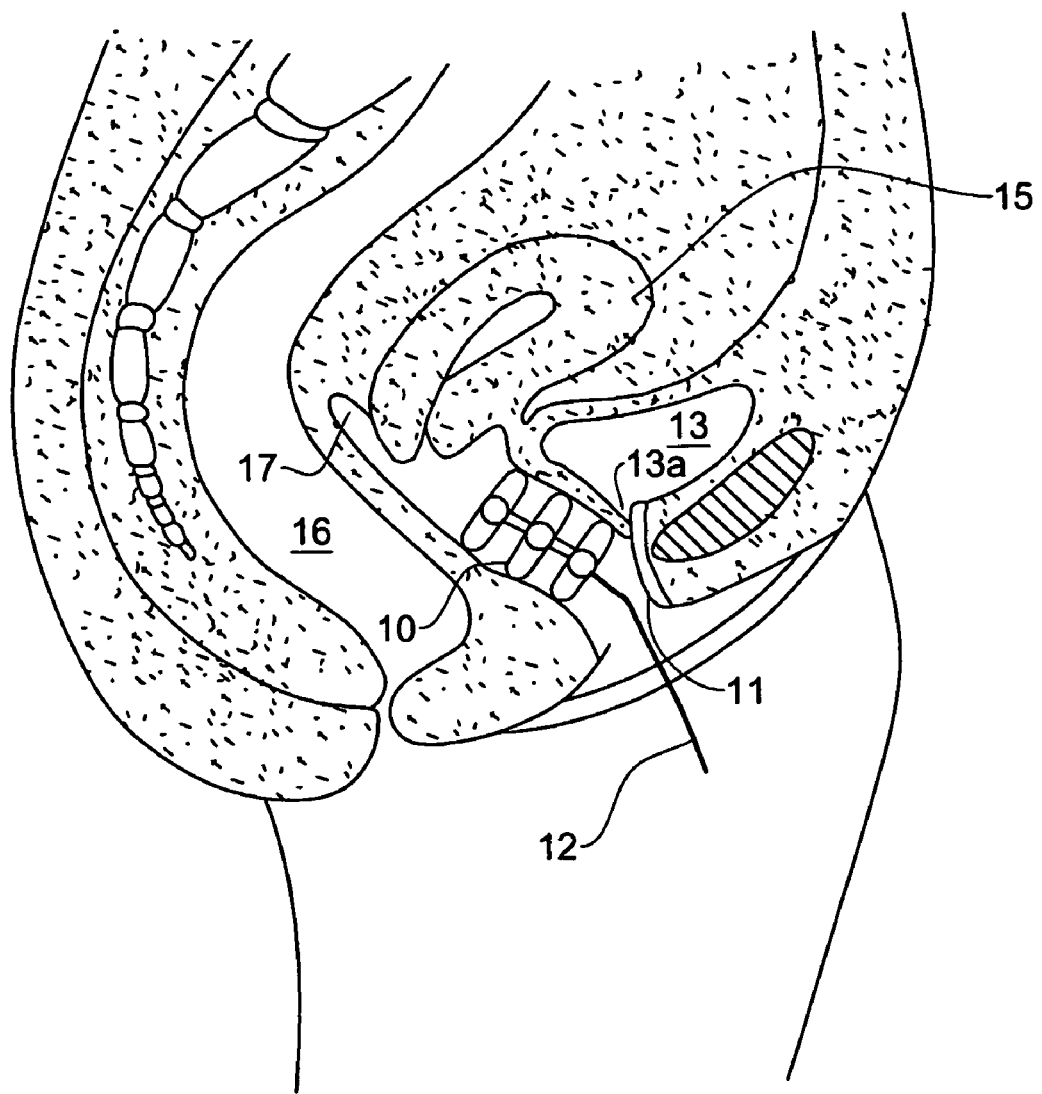
FIG. 1 is a schematic view of the pelvic floor region of the female body, with one embodiment of the device for treating urinary incontinence inserted into the vagina.

Referring first to FIG. 1, a device (10) for treating urinary incontinence is shown after being inserted into the vagina (14) via an applicator. A string (12) extends from the vaginal opening so as to allow the woman to easily remove the device (10) by pulling gently on the string (12). In usage, the device (10) applies pressure on the walls of the vagina increasing their tensile strength against the pelvic floor thus providing support for the bladder neck (13a) and for the urethra (11) whenever the bladder neck and urethra descends to a lowered position towards the anterior wall of the vagina due to some damage to the support mechanism that otherwise maintains said bladder neck and urethra in a raised position. The particular preferred embodiment illustrated in FIG. 1 will be further described in FIGS. 5a-5d.

It will be appreciated that certain preferred embodiments of the present invention may be useful not only for the treatment of urinary incontinence, but for the treatment of pelvic organ prolapse as well. This includes prolapse of urethra (11) (urethrocele), prolapse of the bladder (13) (cystocele), prolapse of the posterior formix (17) (enterocele), and prolapse of the posterior vaginal wall with the rectum (16) (rectocele). When ligaments that hold the uterus (15) in place weaken, uterine descent occurs. In cases where the uterus has been surgically removes, and the vagina is dome-shaped, a vault prolapse may occur. By providing support for the walls of the vagina, the device of the present invention may offer a practical and easy solution for many of the aforementioned conditions.

It is appreciated that all preferred embodiments of the present invention comprise an internal support structure composed of spaced apart pressure providing member and anchoring member and optionally a cover made of a sufficiently flexible material that substantially completely surrounds said internal support structure both before and after the device is inserted into the vagina. In the description herein provided, the "device" is meant to refer only to the internal support structure and optionally to the accompanying cover, since these are the two components which remain in the vagina following insertion of the device using an applicator. In the detailed description provided, the term "device" is not meant to include the applicator and the plunger which according to the definition are part of the system of the invention.

Figure 2A:
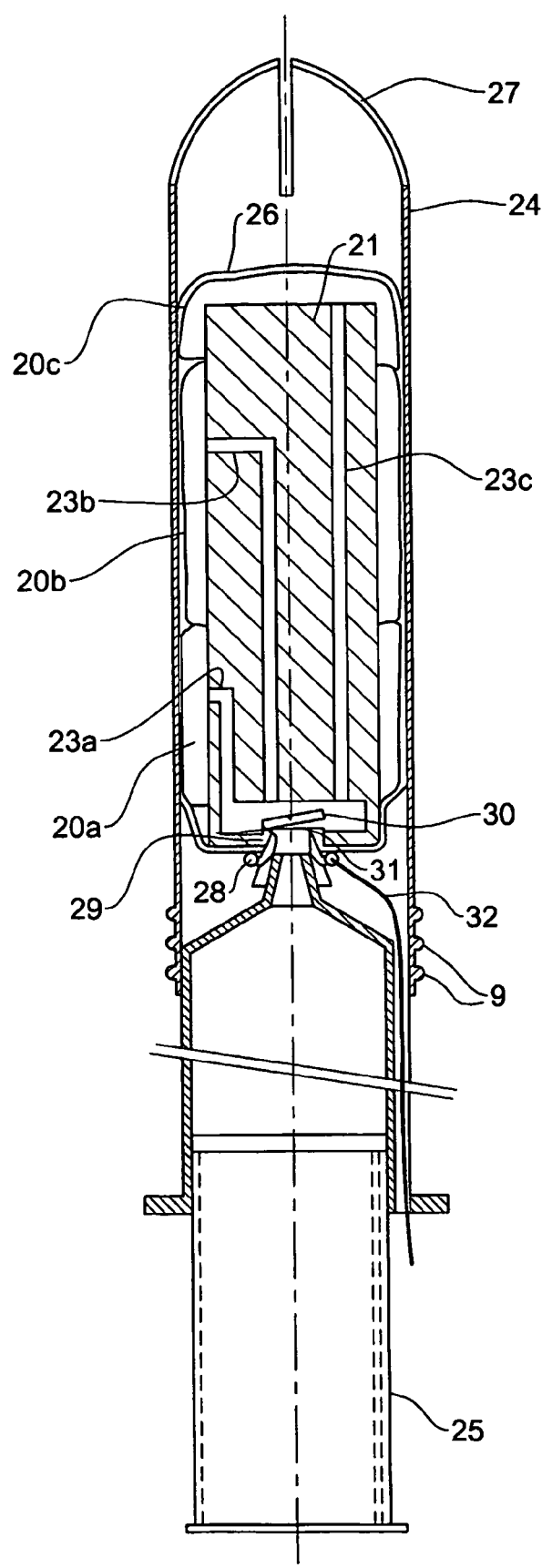
FIGS. 2a and 2b illustrate cross-sectional side views of an embodiment for a device of the present invention that operates through pneumatic means. The device is shown inside of the applicator, prior to insertion into the body (FIG. 2a) and following activation, after insertion into the vagina (FIG. 2b).
Figure 2B:
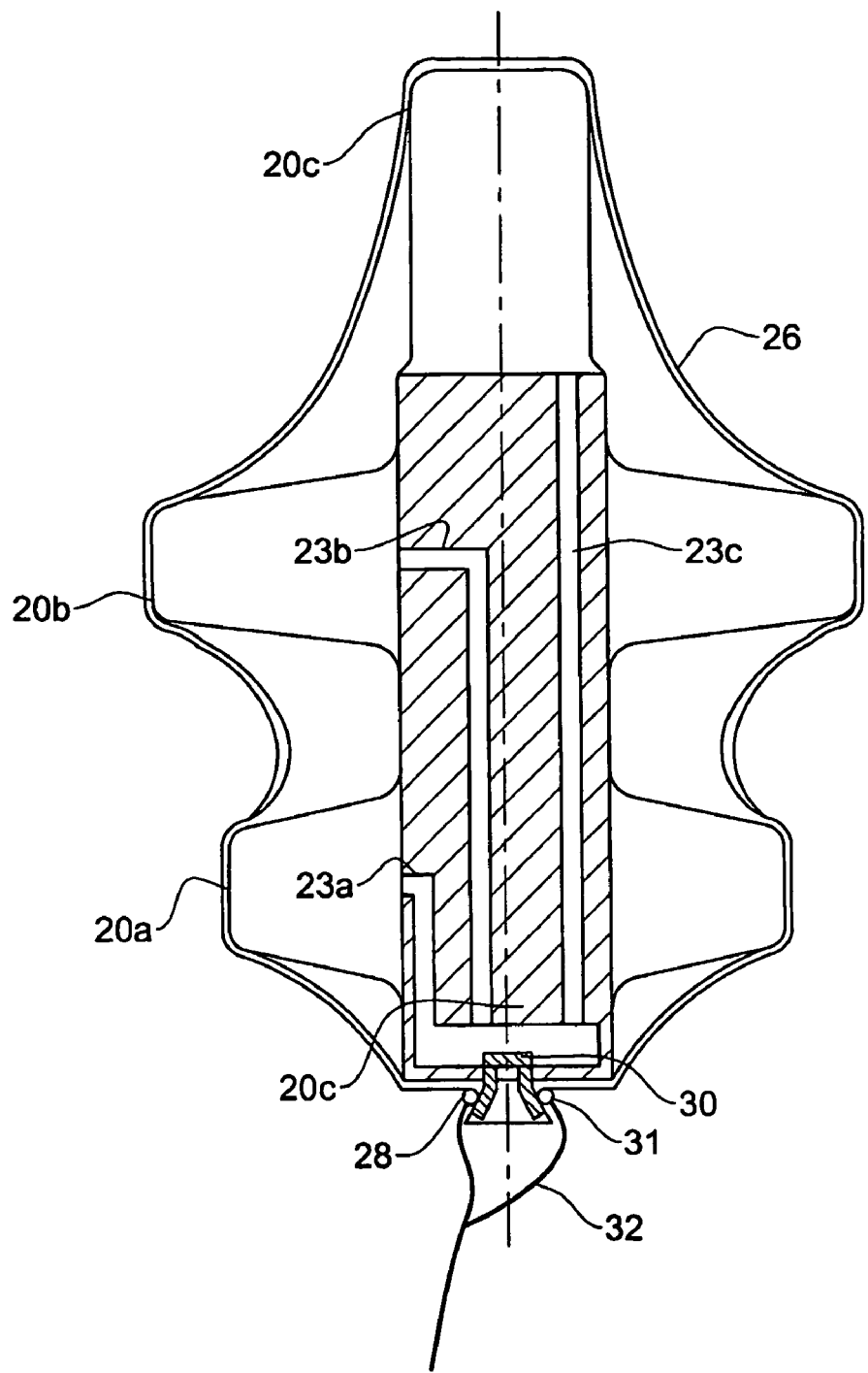

Reference is now made to FIGS. 2a and 2b, and to a first preferred embodiment of the present invention. The device illustrated is comprised of an internal support structure comprising three inflatable balloons (20a, 20b, 20c) each attached along the outer surface of a support body (21). The balloons may be comprised of any suitable expanded material known in the art, and they may be inflated using any fluid such a suitable gas (as air) or any other suitable gas or liquid medium. It is also appreciated that while the preferred embodiment illustrated has three balloons, the device may comprise any number of balloons, preferably between 1 and 3. Where the device comprises a single balloon it serves as an integrated construction comprising both the pressure providing member and the anchoring member.—The use of inflatable balloons facilitates the insertion of the device in an "inactive" and compact configuration, while providing sufficient support for the vaginal walls following expansion into the active configuration. By using three balloons, three different goals are accomplished: the urethra is supported (this is accomplished by the first balloon (20a)); the device is anchored into place (this is accomplished by the middle balloon (20b)); and backwards movement of the device is avoided (this is accomplished by the third balloon (20c)). In usage, each balloon is inflated through a separate inflation passageway (23a, 23b, and 23c, correspondingly) located in the support body (21). Inflation takes place immediately after the device is inserted into the vagina. Prior to insertion, the device is housed inside of an applicator (24) that is operably coupled to a plunger (25). To insert the device, the user presses on the plunger (25) such that the device (the internal support structure and the accompanying cover (26)) protrudes from the anterior end (27) of the applicator (24). Once the internal support structure has become fully extended from the applicator, the plunger (25) is pushed further so as to result in inflation of the three balloons (20a, 20b, 20c), as shown in FIG. 2b. In the applicator illustrated in FIG. 2a, as well as in further applicators that are to be illustrated in the drawings, a plurality of protrusions (9) are preferably provided on the lower external surface of said applicator for facilitating gripping by the user.

It is appreciated that the balloons are sized in accordance with their respective locations inside of the vagina and the support that is desired at each location. The first and second balloons (20a, 20b) are oriented in a manner perpendicular with respect to the support body (21) whereas the third balloon (20c) is oriented so as to extend in a forward manner from the end of the support body (21). In some preferred embodiments, the balloons are substantially tubular shaped, though a variety of suitable shapes could be employed. Moreover, in some preferred embodiments, the balloons have one or more openings extending therethrough so as to allow for the natural flow of vaginal secretions.

In the preferred embodiment illustrated, a flexible one-way valve mechanism (28) is employed for facilitating inflation of the balloons of the device. The valve mechanism is comprised of a flexible valve (29), a valve cover (30), an elastic ring (31) surrounding said valve (29), and a release string (32) coupled to said elastic ring (31). Following inflation of the three balloons, the pressure inside of the balloons prevents the backward flow of air and maintains the balloons in an inflated state. However, when the device is to be removed from the vagina, the user pulls on the release string (32), resulting in the slight distortion of the shape of the valve (29), thereby allowing for the escape of the air from inside of the balloons (20a, 20b, 20c). It is appreciated that other suitable valve mechanisms could also be employed for achieving similar results. The valve that has been described has the advantages of being both inexpensive and simple to use.

Figure 3A:
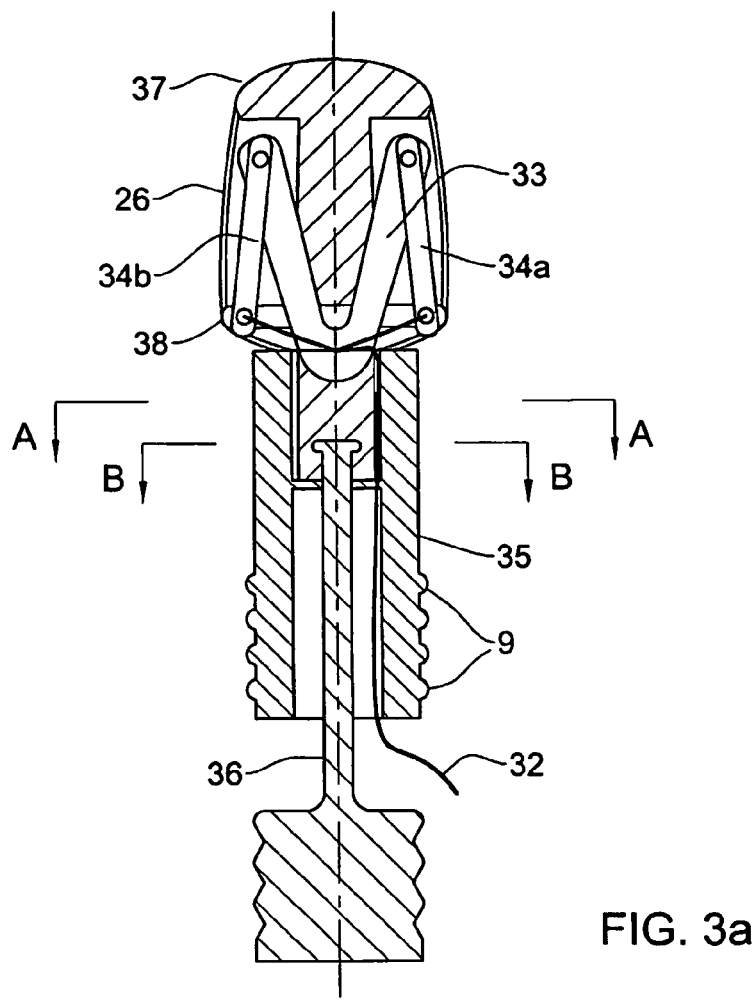
FIGS. 3a, 3b, 3c, 3d, and 3e illustrate a preferred embodiment of the device of the present invention that operates through mechanical means.
Figure 3B:
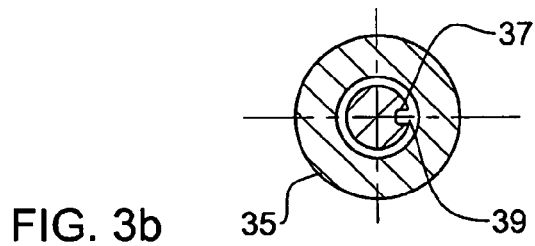
Figure 3C:
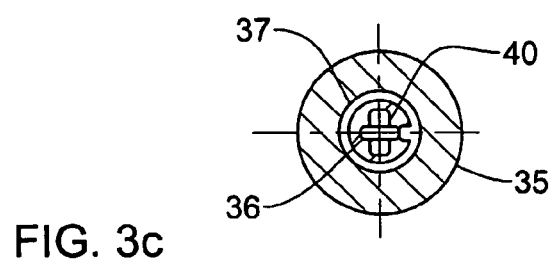
Figure 3D:
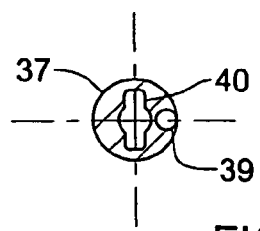
Figure 3E:
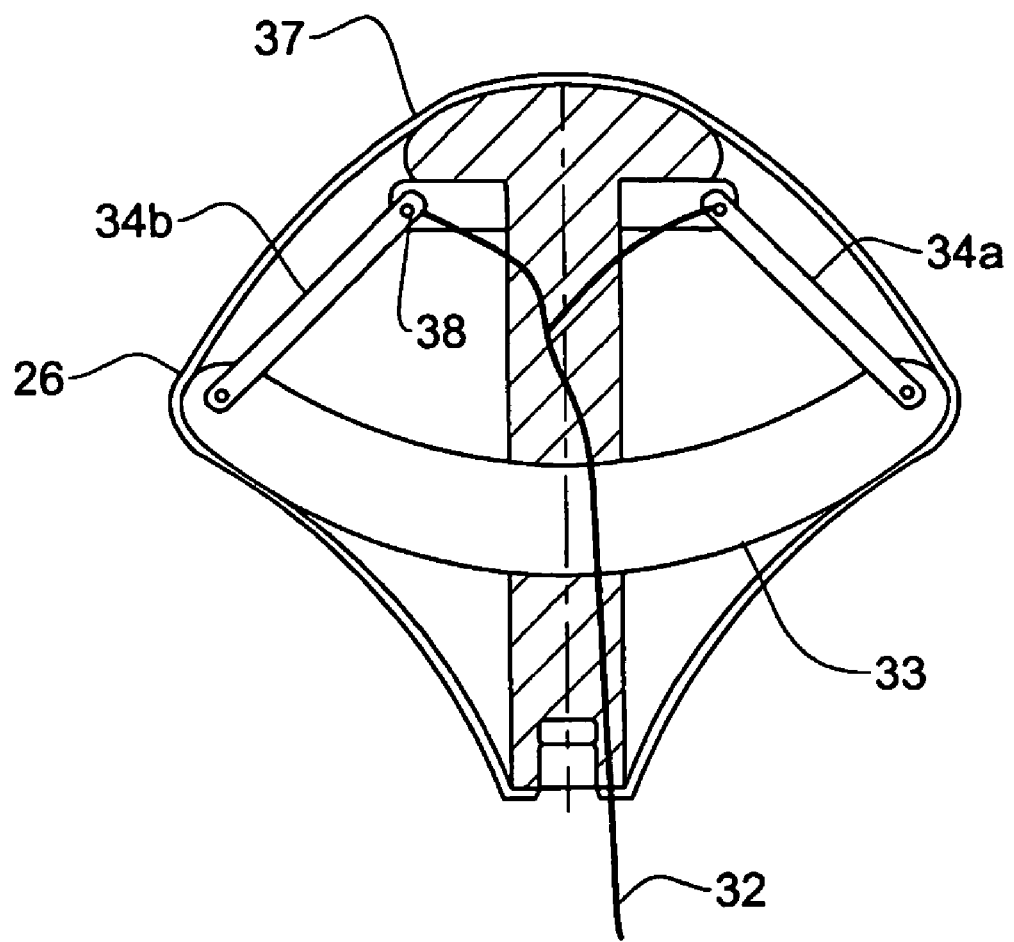

Reference is now made to FIGS. 3a-3e and to another preferred embodiment of the present invention. This preferred embodiment functions via mechanical means. The device illustrated comprises an internal support structure that includes a flexible expanded support arc (33) and two support arms (34a, 34b) operably coupled to said support arc (33). The support structure further comprises an elongate body (37) and an actuating ring (38). Surrounding the support structure is a cover (26). Insertion of the device into the body is facilitated by the use of an applicator (35) and an active plunger (36), both of which are removed from the rest of the device after the insertion and activation of said device. A release string (32) allows for collapsing of the support structure after usage so as to enable its removal from the vagina by pulling at the actuating ring 38 thereby causing collapse of support arc 33. FIG. 3b is a cross-section through line A-A of FIG. 3a, showing a small opening (39) extending through the elongate body (37). The release string (32) extends though said small opening (39). During insertion of the device, the active plunger (36) is pushed inward against the lower end of elongate body (37), to which it is removably engaged. This action results in the shifting of the actuating ring (38) from a lowered position (see FIG. 3a) to a raised position (FIG. 3e), which is accompanied by the outward movement of the support arm (33) and corresponding movement of the support arms (34a, 34b)). As the support arc (33) is expanded, the cover (26) stretches so as to accommodate the support arc. Once in an activated configuration, the user rotates the active plunger (36) by 90 degrees, thereby enabling removal of said plunger from the rest of the device. FIG. 3c is a cross-section through line B-B of FIG. 3a, prior to the removal of the plunger and applicator. FIG. 3d is a cross-section through line B-B of FIG. 3a, after removal of the plunger and applicator. The end of the plunger (36) is contoured such that it cannot be removed from the device until rotation takes place. During rotation, said end of the plunger (36) becomes aligned with a groove (40) inside the elongate body (37) that is of a shape complimentary to said end of the plunger (36) such that the plunger can be withdrawn from the elongate body (37) via the groove (40).

By another alternative actuating the support arms are made of flexible material and are integrated with the wall of the elongated body so they may collapse upon application of external pressure on the elongated body (such as inside an applicator) and expand upon relieve of the external pressure.

Figure 4A:
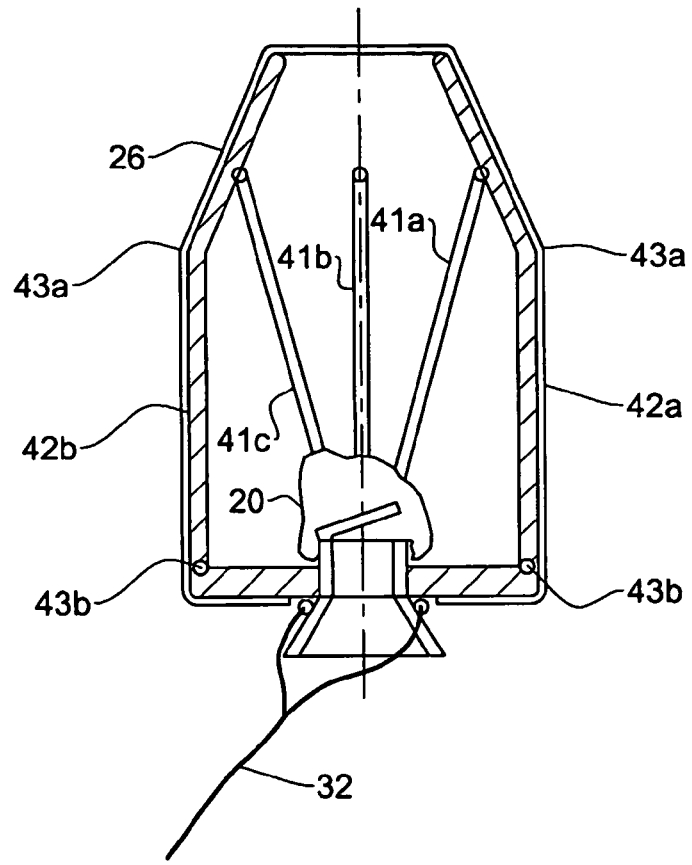
FIGS. 4a and 4b illustrate schematic side views of an embodiment of the device of the present invention that operates through pneumo-mechanical means.
Figure 4B:
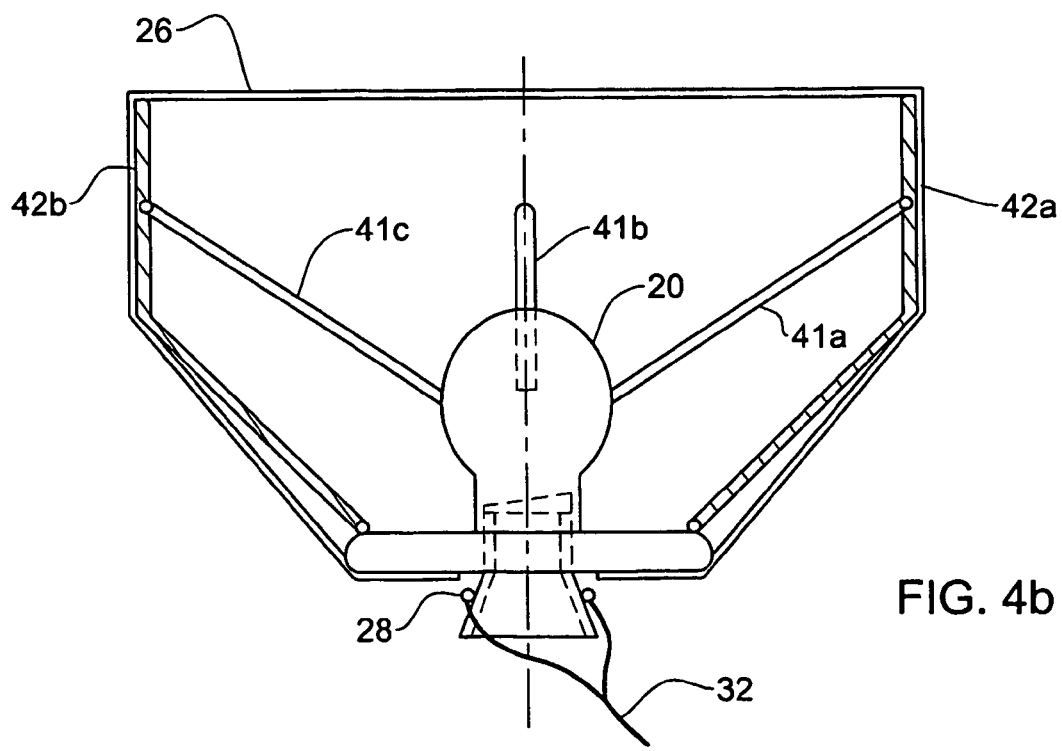

Referring now to FIGS. 4a and 4b, the device illustrated is comprised of a support structure that includes an inflatable balloon (20), four arms that extend from said balloon (three of which are visible; 41a, 41b, 41c), and four support members (two of which are visible; 42a, 42b) coupled to the ends of said arms. The device further includes a cover (26). The inflatable balloon (20) may be inflated (and deflated) via the flexible valve mechanism (28) which was described in detail in FIGS. 2a and 2b. Other suitable mechanisms could also be employed. Furthermore, the applicator that is used is preferably the same as the applicator described in FIGS. 2a and 2b. Prior to insertion of the device into the vagina, the arms (41a, 41b, 41c) are positioned in a non-extended configuration. Inflation of the balloon (20) results in outward movement of the arms (41a, 41b, 41c) to an extended configuration. When the arms (41a, 41b, 41c) extend, they push against the support members (42a, 42b) and cause said support members to become expanded. Said support members (42a, 42b) expand outward via two pivot points (43a, 43b) located along the length of said support members (42a, 42b). It is appreciated that while the preferred embodiment illustrated comprises a single balloon operably coupled to four support members, other preferred embodiments are possible. For example, the device could comprise three balloons positioned one after the next on an elongate body, wherein each balloon has at least two support members operably coupled thereto, said support members being adapted for expanding when the balloons are inflated.

Figure 5D:
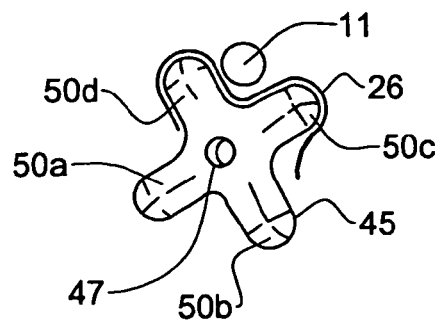

Reference is now made to FIGS. 5a-5d and FIGS. 6a-6c in order to illustrate another preferred embodiment of the present invention. The device illustrated comprises a plurality of star-shaped members (45a, 45b, 45c) that are interconnected via an elongated body (46) that extends through an opening (47) located in the center of each star-shaped member. The elongated body (46) may be comprised of a substantially rigid material (FIG. 5a) or it may be comprised of a flexible material (FIG. 5b) which has the advantage of allowing the device to conform to the curvature of the vaginal canal. While the device illustrated comprises three star-shaped members, it is appreciated that any other suitable number is possible as well, preferably between 1 and 3. In FIG. 5c, the cover (26) is illustrated covering the star-shaped members (45a, 45b, 45c), and in FIG. 5d, it is possible to see the manner in which the cradle support for the urethra (11) is provided by the star-shaped members in conjunction with the cover. Preferably, each star-shaped member comprises four prongs (50a, 50b, 50c, 50d), though it is appreciated that a three, five, or six-pronged star-shaped members could also be employed in certain preferred embodiments.

Figure 6A:
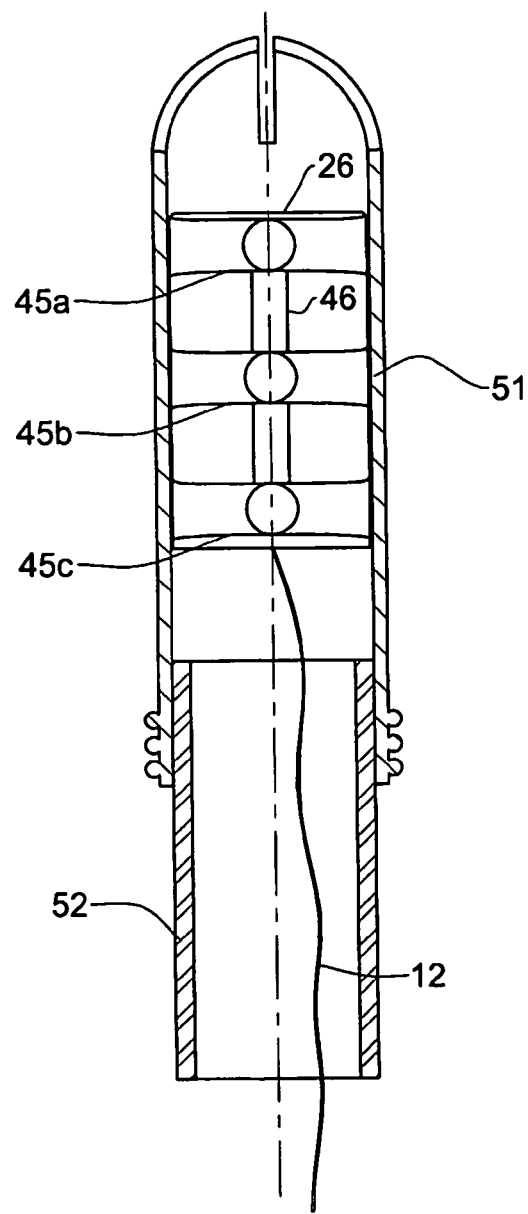
Figure 6B:
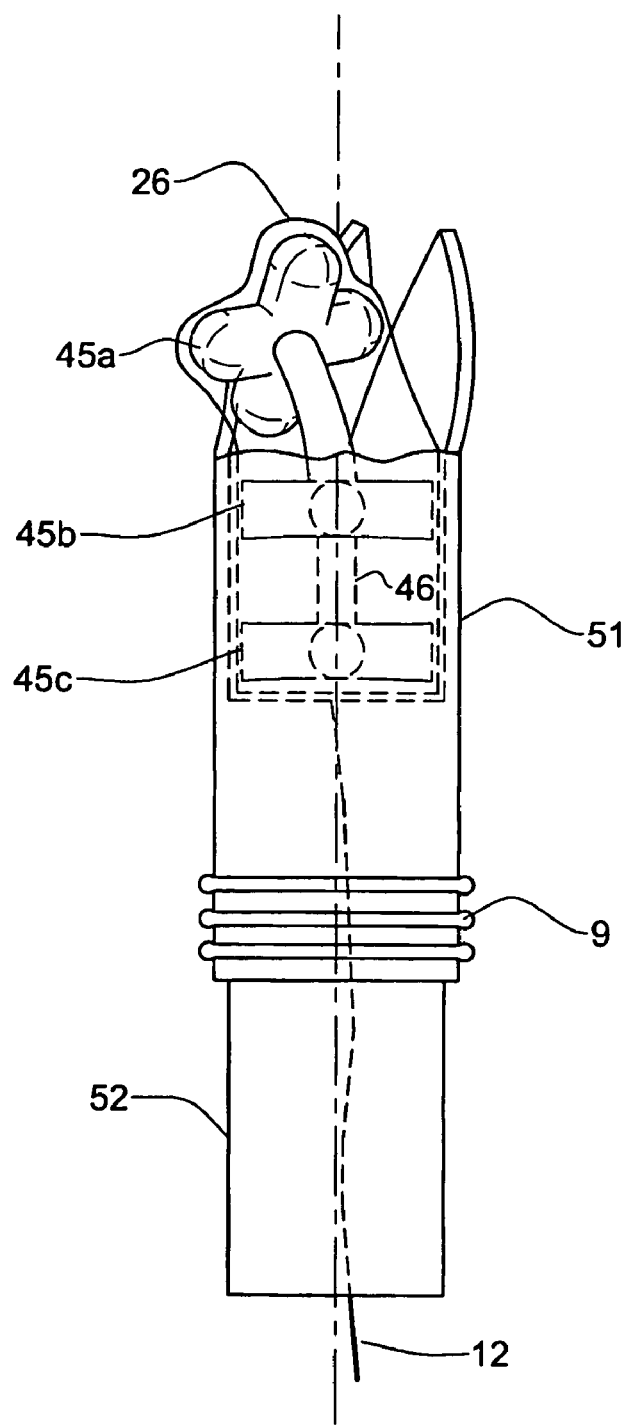
Figure 6C:
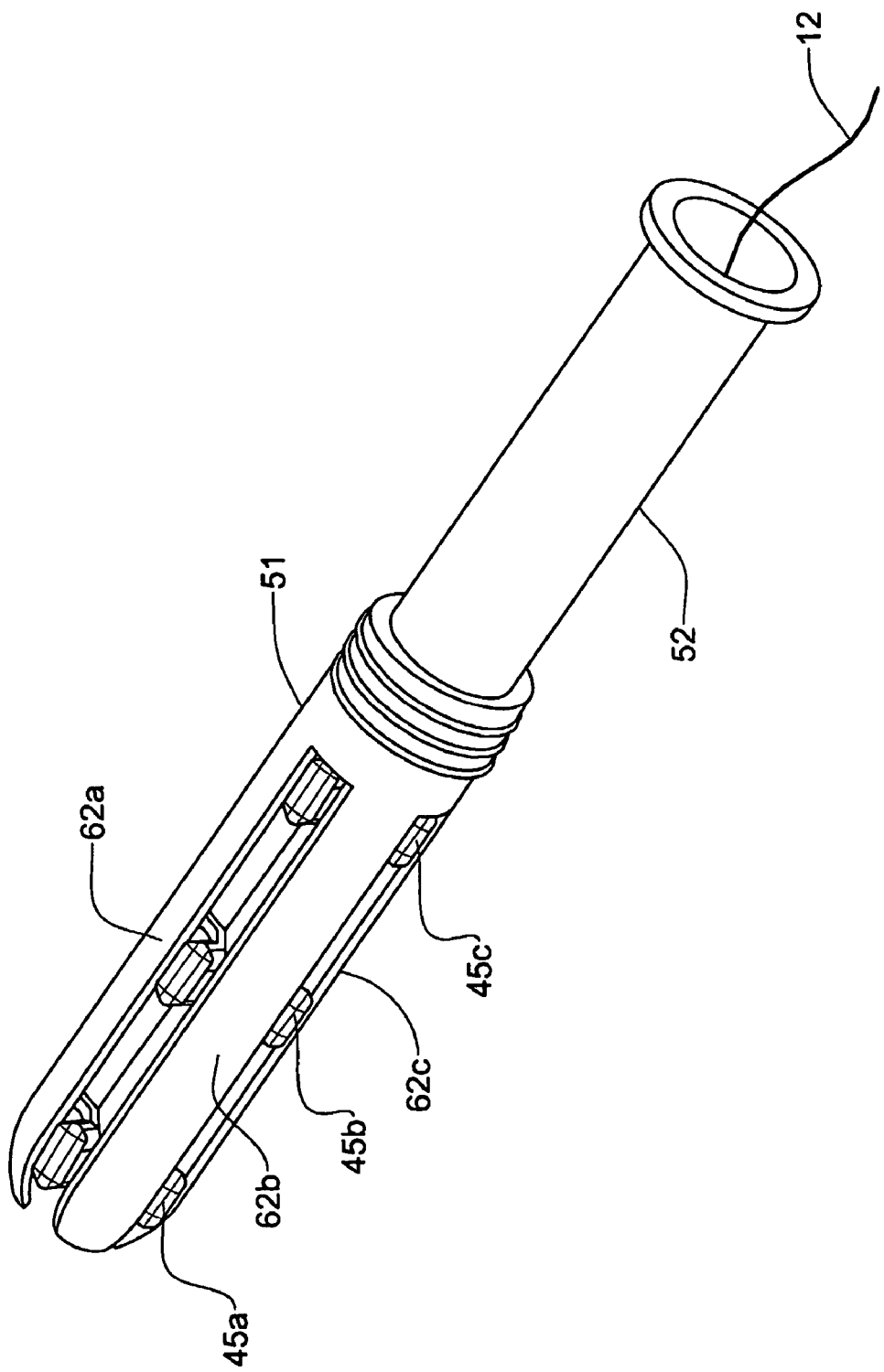

Referring now to FIGS. 6a and 6b, prior to insertion of the device into the vagina, the star-shaped members (45a, 45b, 45c), the elongated body (46) on which they are held, and the accompanying cover (26), are housed inside an applicator (51). The applicator (51) illustrated operates in the same manner as a (menstrual period) tampon applicator, as are well known in the art. To insert the device, the user simply pushes on the plunger (52) until the device (the internal support structure and the cover) becomes released from the applicator (51) and positioned in the vagina. A release string (12) is provided for allowing removal of the device. In the preferred embodiment illustrated in FIG. 6c, the applicator (51) is specially designed with four gripping elements (three of which are seen; 62a, 62b, 62c) for gripping the prongs (50) of the star-shaped members (45a, 45b, 45c).

Figure 7A:
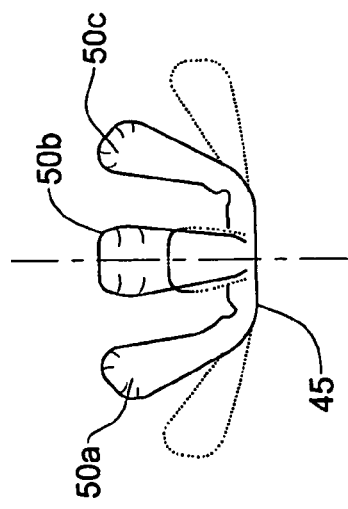
FIGS. 7a-7d and FIG. 8 illustrate another preferred embodiment of the device of the present invention that is similar to the device illustrated in FIGS. 5a-5d and FIGS. 6a-6c.
Figure 7C:
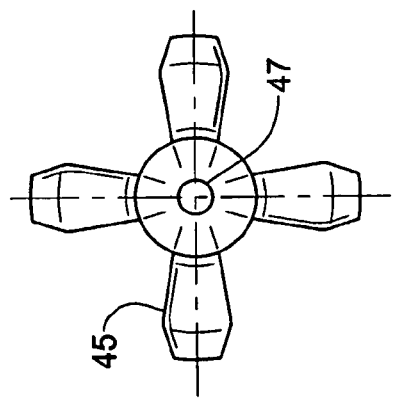
Figure 7B:
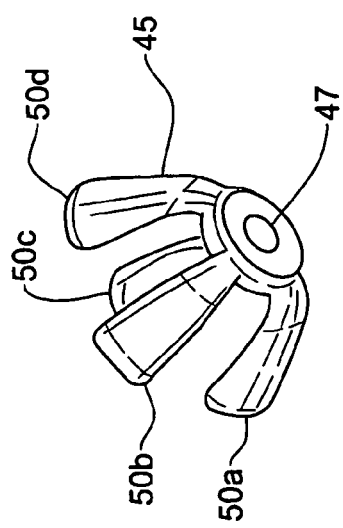
Figure 7D:
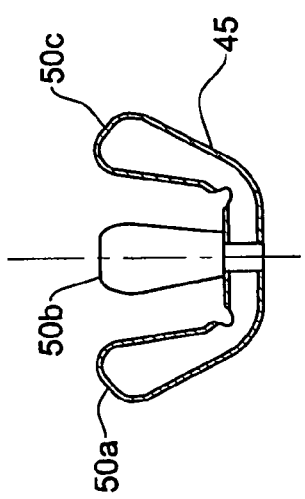
Figure 8:
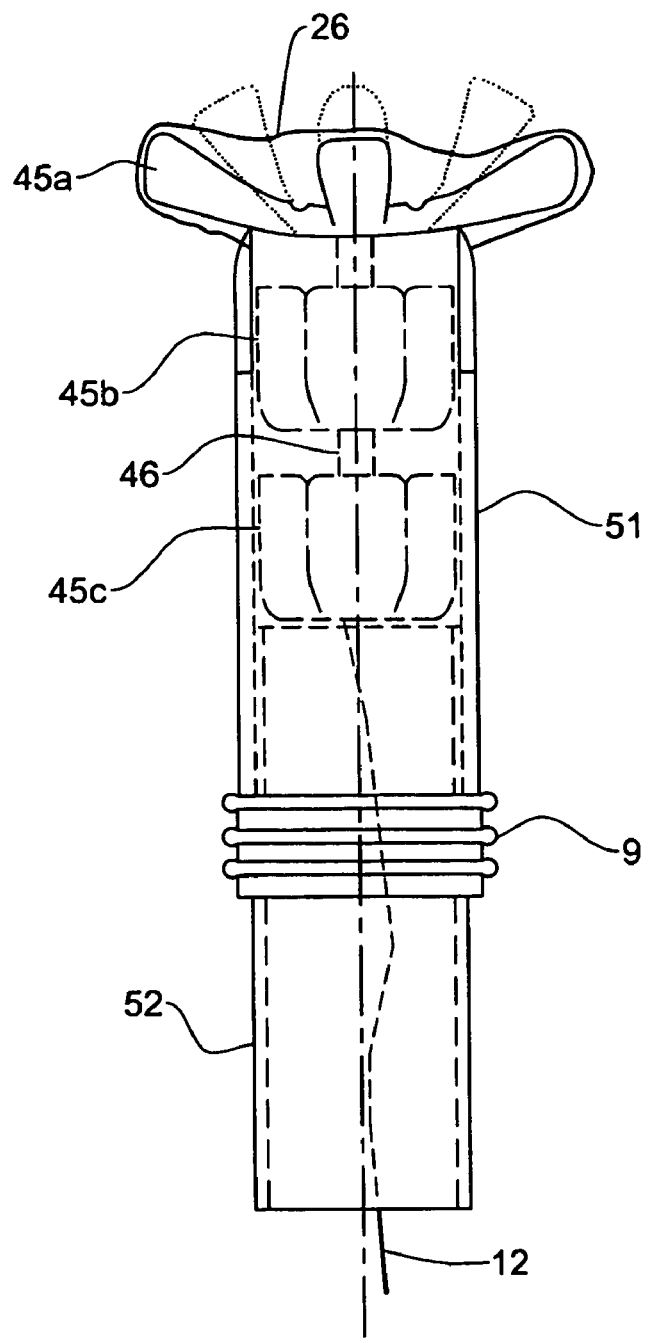

The preferred embodiment illustrated in FIGS. 7a-7d and FIG. 8 is similar to the preferred embodiment that was described in FIGS. 5a-5d and FIGS. 6a-6c, and thus all numerals used in the drawings which are not directly referred to here should be assumed to refer to the same features as in the previous Figures. The device comprises a plurality of star-shaped members (45). The main difference between the preferred embodiments is that in this device the star-shaped members are highly flexible, and thus, they are housed inside the applicator (51) in a compressed, "inactive" configuration (see star-shaped members 45b, 45c of FIG. 8) due to the pressure of the inner walls of the applicator (51) on the prongs of the star-shaped members. As the device is pushed out from the applicator (51), the star-shaped members (45) automatically assume an extended configuration (see star-shaped member 45a of FIG. 8) due to the elastic force. In FIGS. 7a and 7b, the star-shaped member (45) is in a "compressed" position. In FIG. 7c, the compressed and the extended, "active" configuration can be seen. In FIG. 7d, the star-shaped member (45) is illustrated extended, as it would be inside of the vagina. The applicator (51) of FIG. 8 functions in the same manner as the applicator that was described in FIGS. 6a and 6b. The device can be easily removed from the vagina using the release string (12), since, upon removal, the walls of the vaginal opening will cause the prongs of the star-shaped members to again compress inwardly towards one another.

It is appreciated that the star-shaped members described in the previous preferred embodiments may be manufactured both with varying degrees of flexibility and with varying sizes, in order to for ease of insertion into the vagina, but to also provide sufficient support for the vaginal walls. While the preferred embodiment of FIGS. 7a-7d and FIG. 8 contains star-shaped members having a relatively high degree of flexibility and the preferred embodiment of FIGS. 5a-5d and 6a-6c contain star-shaped members having a low degree of flexibility, numerous devices could be developed having star-shaped members with any suitable intermediate degree of flexibility as well. Furthermore, it is appreciated that the star-shaped members illustrated in FIGS. 7a-7d and FIG. 8 are oriented such that in the compressed state, the prongs face towards the forward end of the applicator. It is appreciated that the star-shaped members could be oriented in the opposite direction as well, with the prongs of the star-shaped members facing the back of the applicator when in the compressed state. When in an expanded, active state, the prongs may extend at 90 degrees angles with respect to the elongated body on which the star-shaped members are held. However, it is appreciated that said prongs may be adapted for extended outwardly to any appropriate angle with respect to said elongated body. Furthermore, in the preferred embodiment of FIGS. 5a-5d and FIGS. 6a-6c, the star-shaped members need not be oriented strictly at 90 degree angles with respect to the elongated body but may form any suitable angle with said elongated body, and may even be split into sub-prongs, facing different angles.

Figure 9A:
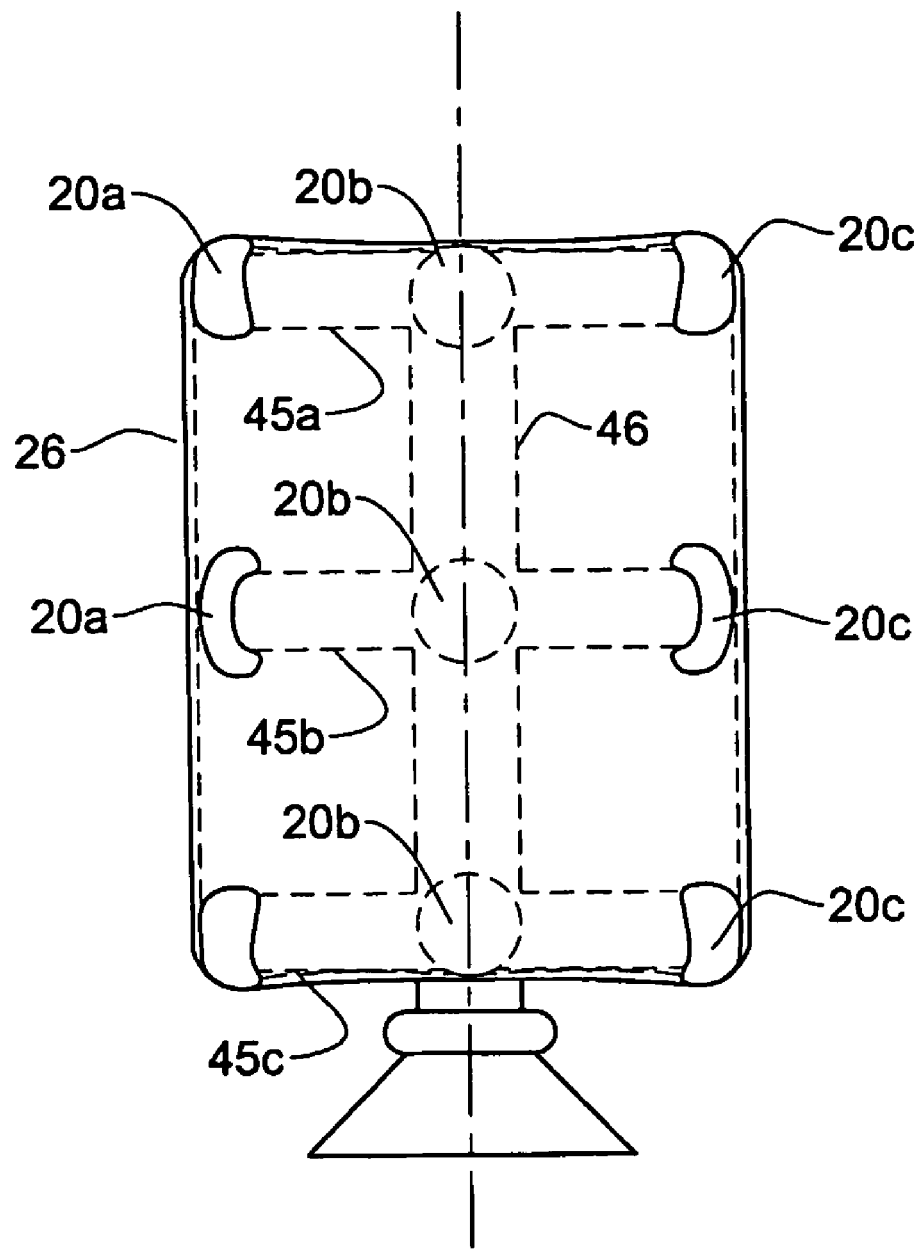
FIGS. 9a, 9b, and 9c illustrate a further preferred embodiment of the device of the present invention.
Figure 9B:
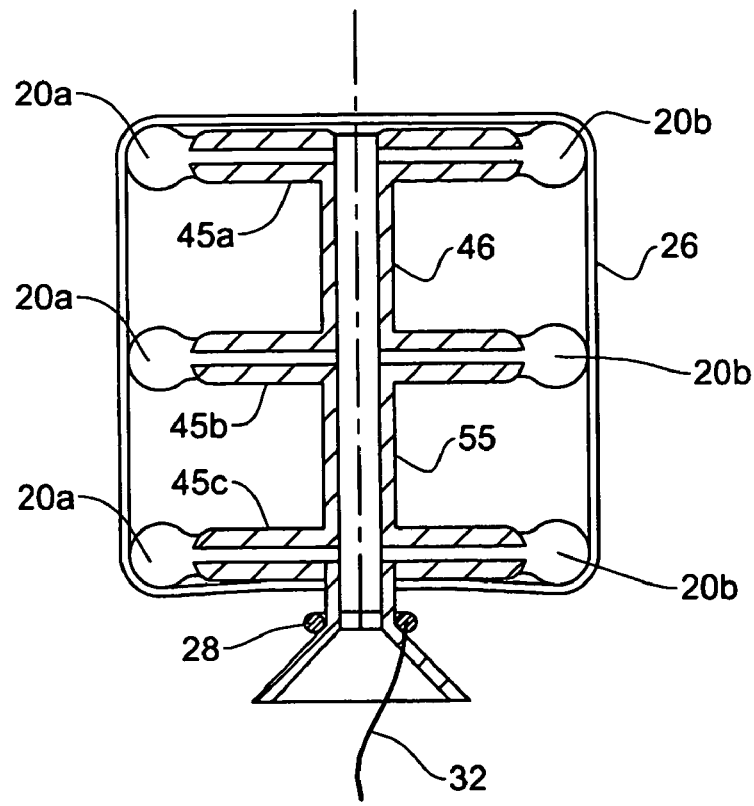
Figure 9C:
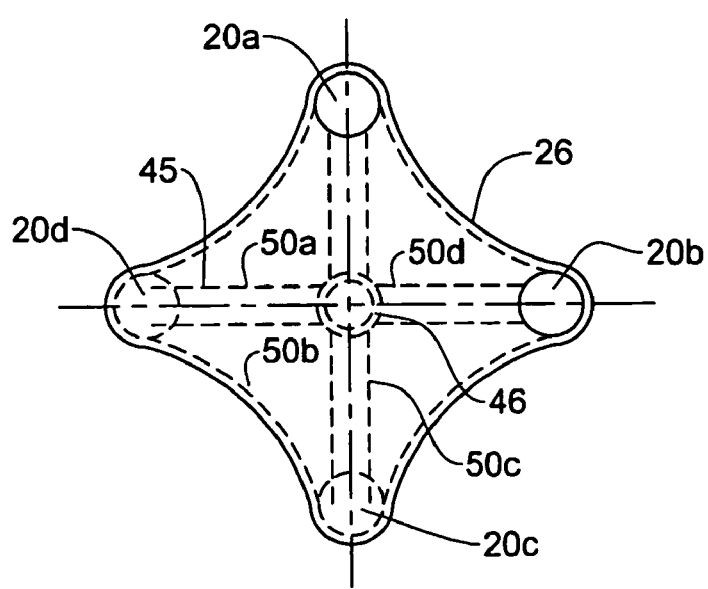

Reference is now made to FIGS. 9a, 9b, and 9c and to a further preferred embodiment of the present invention which employs the star-shaped members (45a, 45b, 45c) of the previous preferred embodiments in combination with a plurality of inflatable balloons (20a, 20b, 20c, 20d). An elongated body (46) made of a flexible material serves to interconnect the star-shaped members (45a, 45b, 45c). Each star-shaped member (45a, 45b, 45c) has one inflatable balloon positioned at the end of each prong thereof. In FIG. 9a, the balloons (20a, 20b, 20c) are illustrated in a non-inflated state, as they appear when the internal support structure of the device is housed inside of the applicator (51) prior to insertion. As seen in FIG. 9b, in the elongated body and extending through to each star-shaped member (45a, 45b, 45c), is a central inflation passageway (55) leading to each balloon (20a, 20b) for allowing inflation of the balloon after the device has been inserted into the vagina. Preferably, inflation is carried out via the flexible valve mechanism (28) that was previously described in FIGS. 2a and 2b. A release string (32), as described in FIGS. 2a and 2b, enables the release of air from inside of the balloons and subsequent removal of the device from the vagina A cross-section of a single star-shaped member (45) can be seen in FIG. 9c, with a balloon (20a, 20b, 20c, 20d) positioned at the end of each prong (50a, 50b, 50c, 50d). The balloons may be adapted for being inflated to any suitable degree, but it is limited by the degree of expandability of the cover (26). The inflated balloons and star-shaped members, together with the cover, serve to form a supportive cradle for the urethra when the device is positioned in the vagina.

Figure 10A:
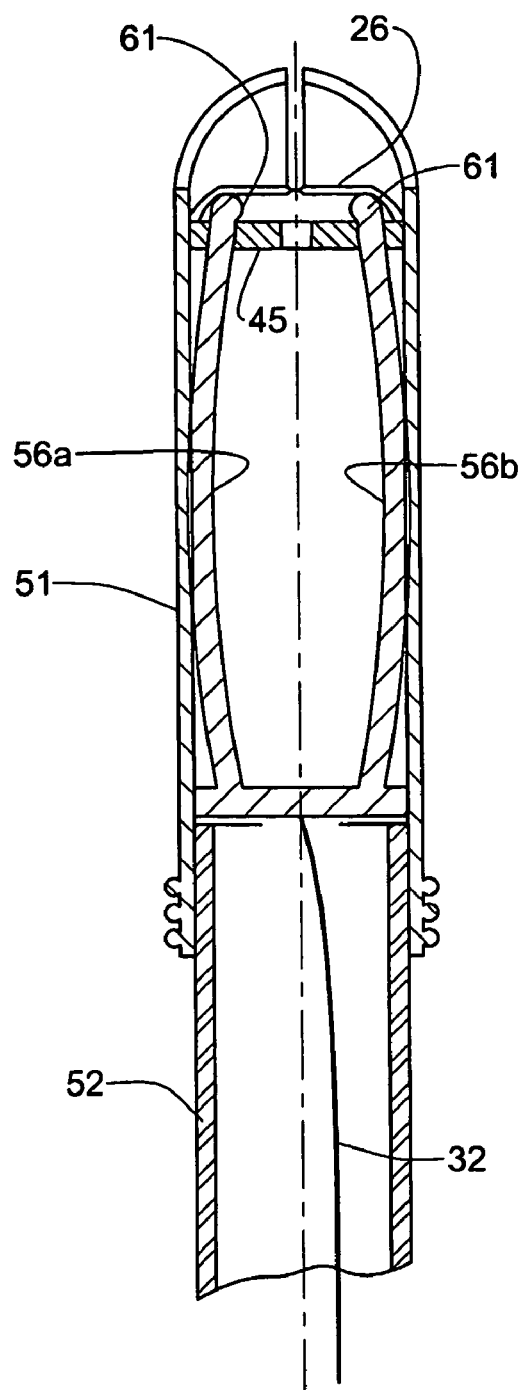
FIGS. 10a, 10b, and 10c illustrate another preferred embodiment of the device of the present invention.
Figure 10B:
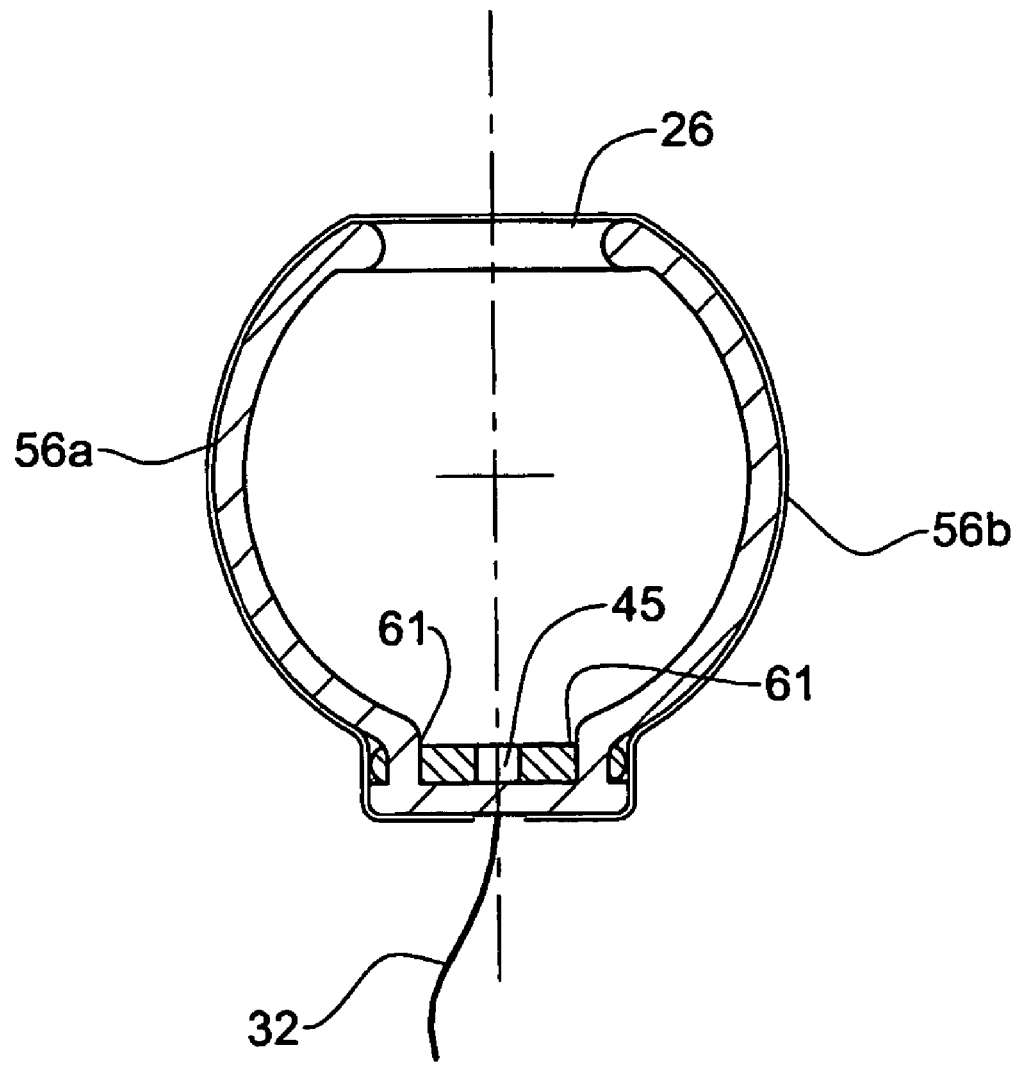
Figure 10C:
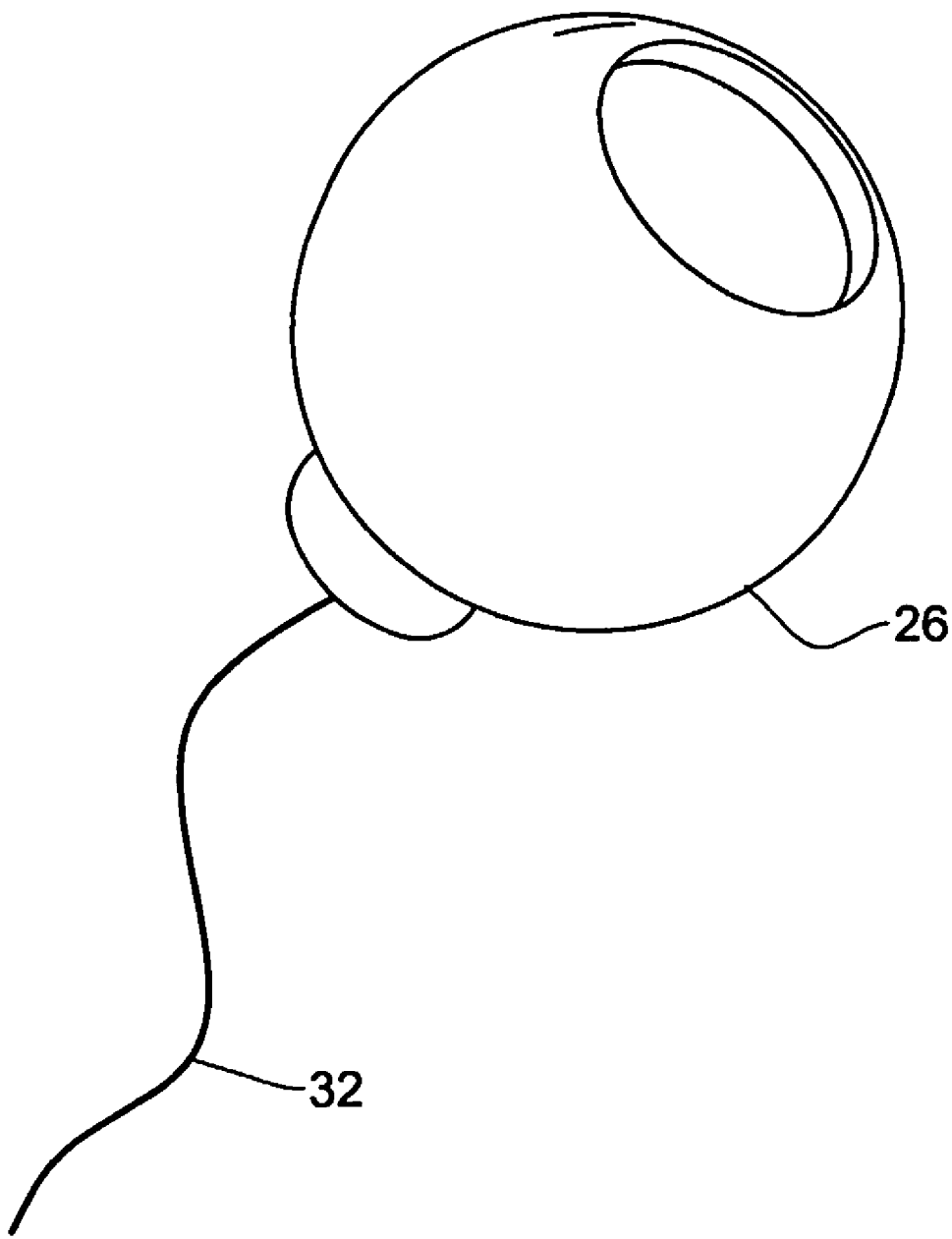

The preferred embodiment shown in FIGS. 10a-10c utilizes a single star-shaped member (45) that is operably coupled to four extending arms (two of which are seen; 56a, 56b) via an opening (61) that exists in each of four prongs of the star-shaped member (45). Initially, when the internal support structure is housed inside of the applicator (51), the star-shaped member is located at the head of the applicator (51) and the extending arms (56a, 56b) are positioned below said star-shaped member (45), with each of the upper ends of the extending arms (56a, 56b) engaged in an opening (61) of the star-shaped member (45) (see FIG. 10a). When the plunger (52) is pushed, the extending arms (56a, 56b) move in the upward direction (through the openings of the prongs) until the star-shaped member (45) becomes fixed at the bottom of the extending arms (56a, 56b), and the extending arms (56a, 56b), the star-shaped member (45), and the accompanying cover are pushed out of the applicator (51). Once extended outside of the applicator (51), the extending arms (56a, 56b) are configured so as to assume an expanded configuration, as seen in FIG. 10b. In the preferred embodiment illustrated, the extending arms (56a, 56b), together with the cover (26), form a substantially spherical body inside of the vagina for providing support of the vaginal walls. It is appreciated that other shapes (for example, oval-like) could be generated depending on the size and arrangement of the extending arms.

Figure 11A:
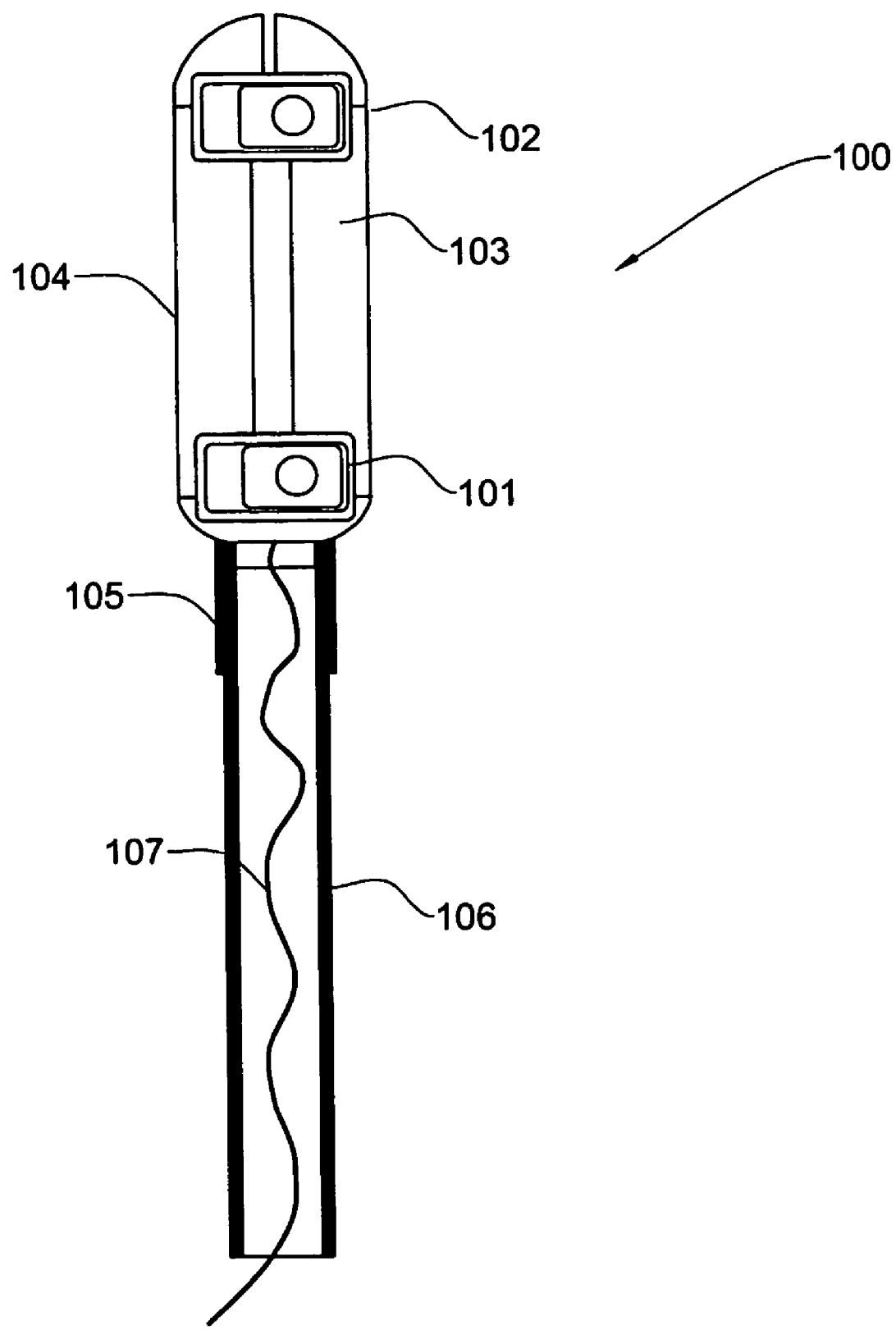
FIGS. 11a, 11b, 11c, 11d, 11e and 11f illustrate another embodiment of the device of the invention.
Figure 11B:
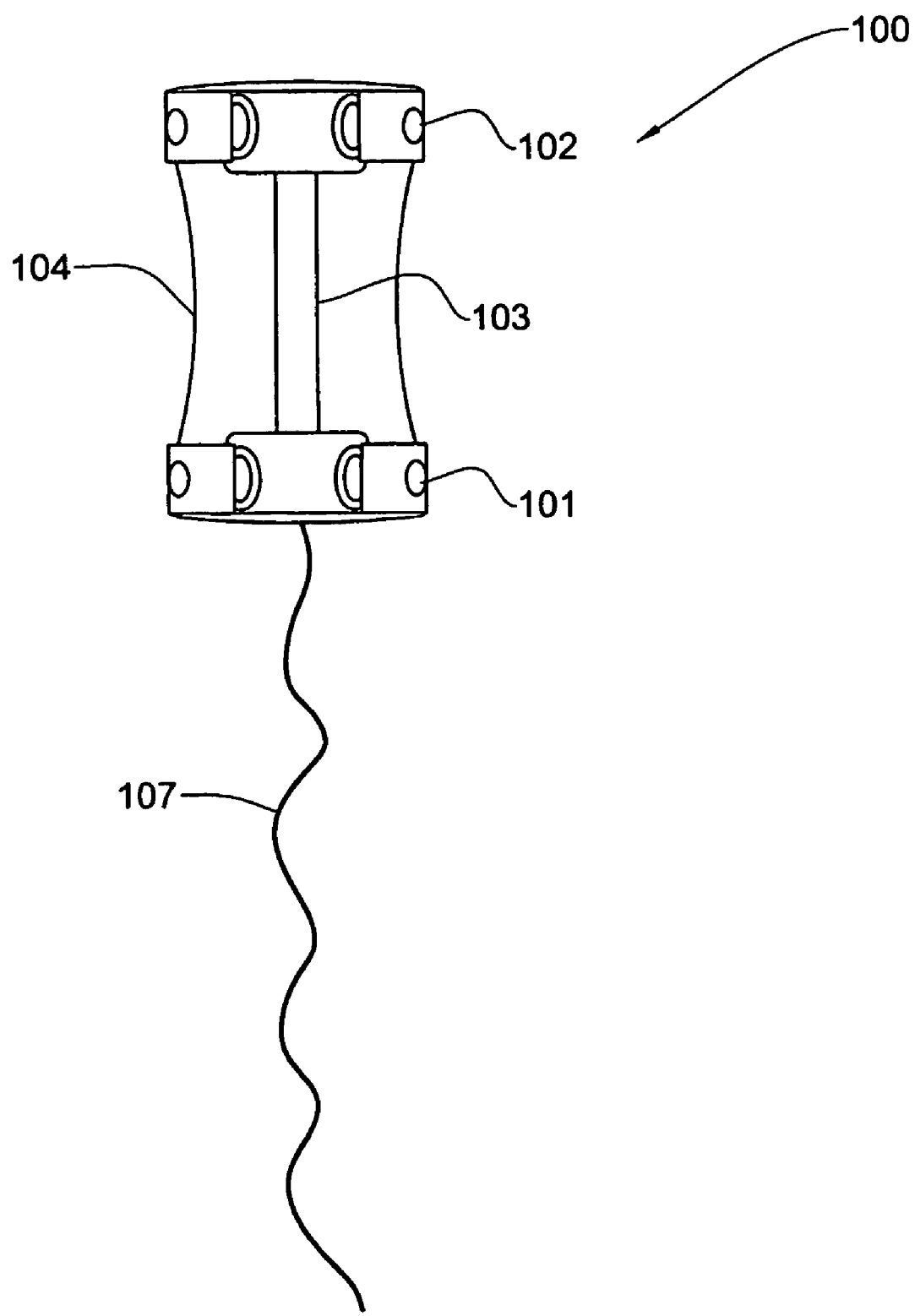
Figure 11C:
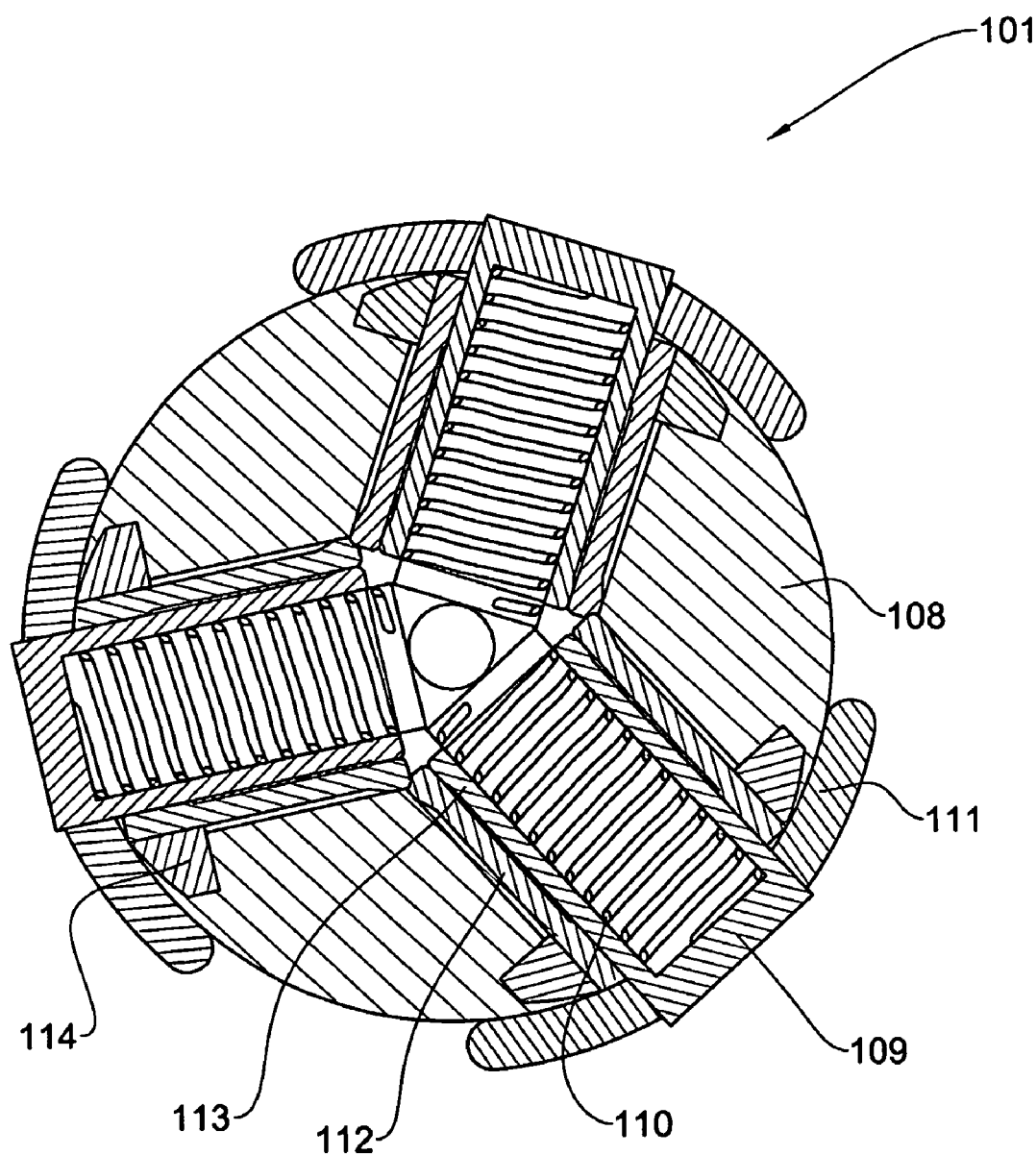
Figure 11D:
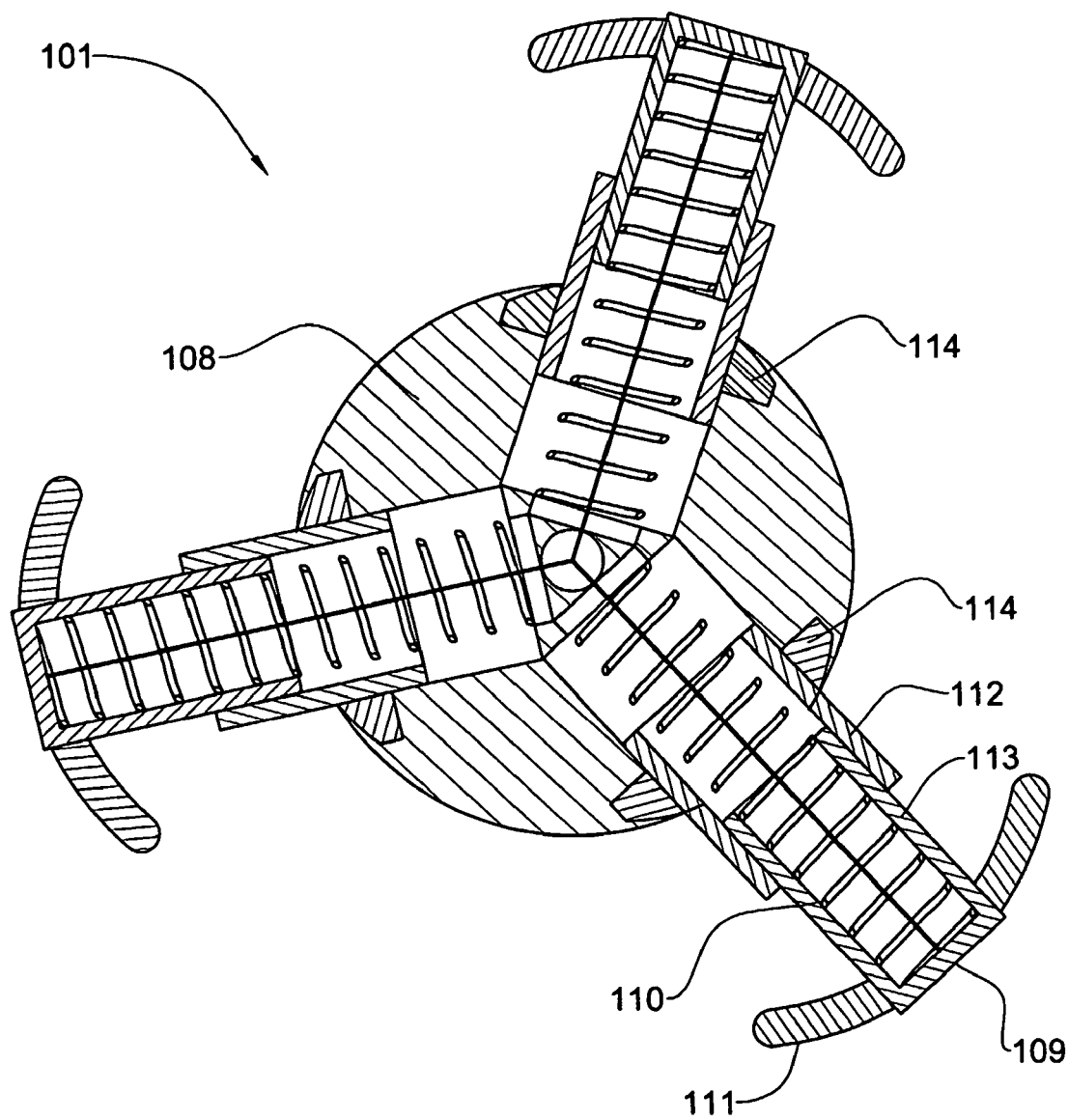
Figure 11E:
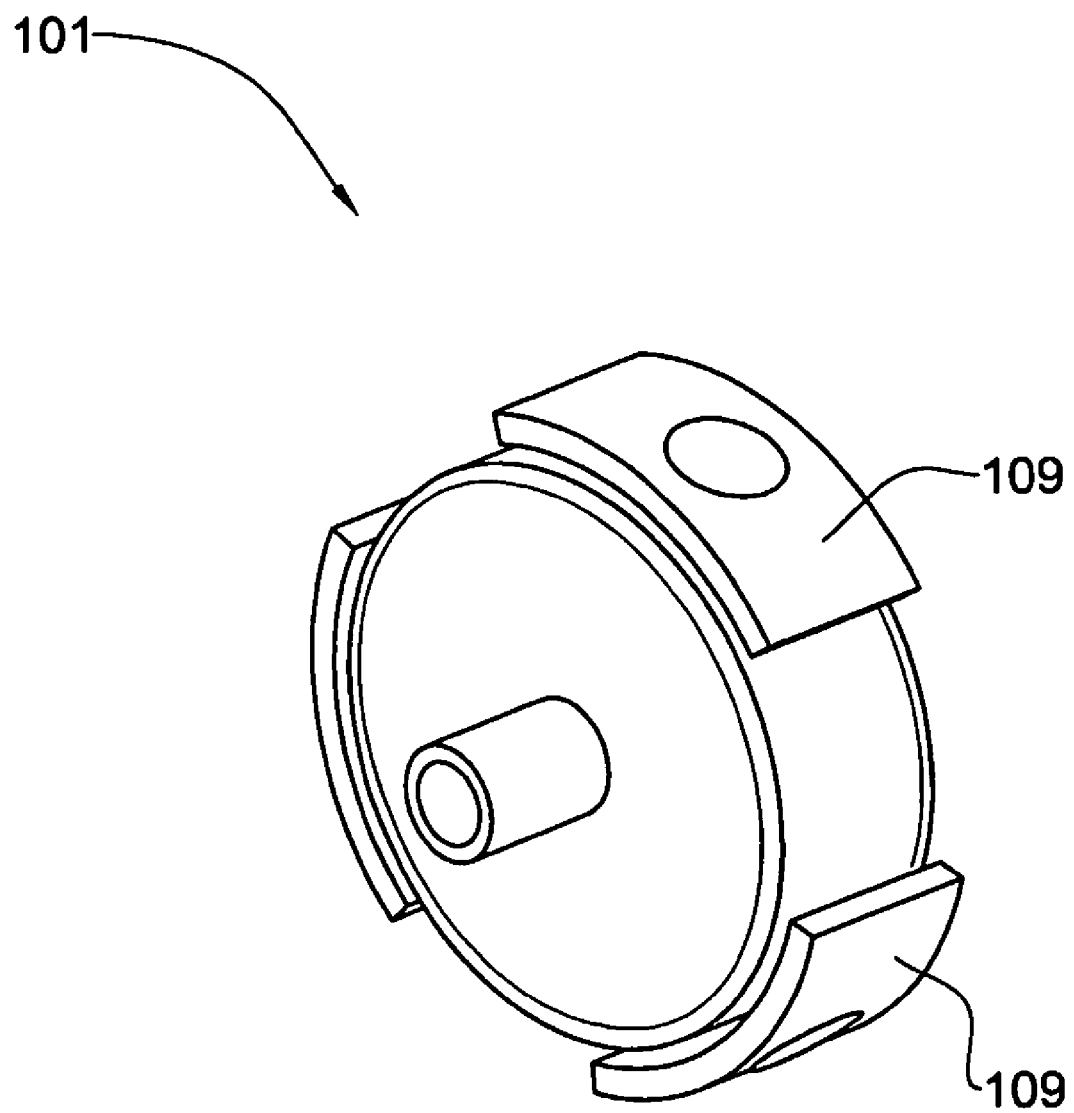
Figure 11F:
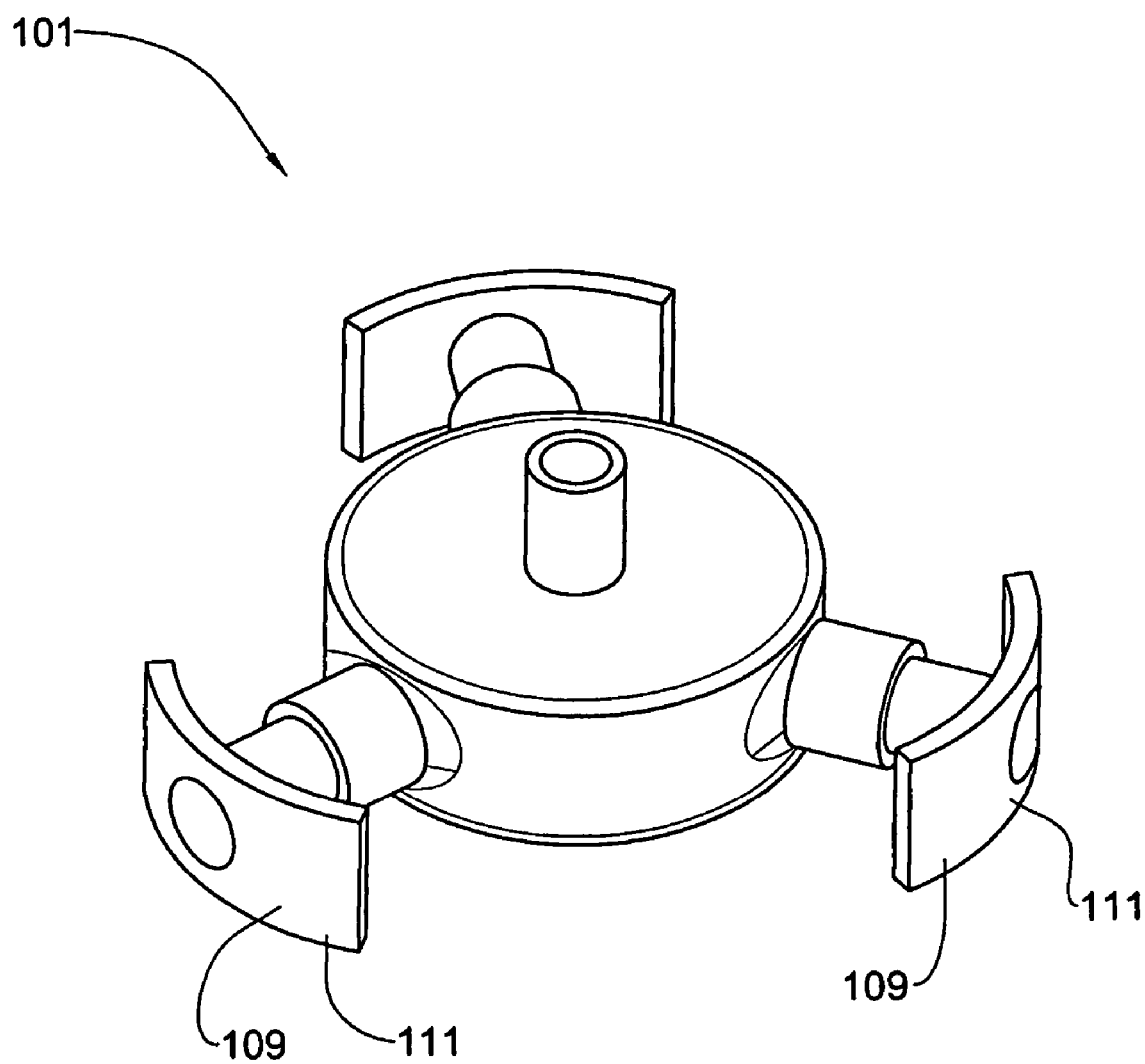

FIGS. 11a, 11b, 11c, 11d, 11e, and 11f, illustrate a device (100) comprising one pressure providing member (101) and one anchoring member (102), both are capable of a transition between a collapsed, closed position as featured in FIGS. 11a, 11c and 11e, said collapsed position suitable for insertion and removal of the device into or from the vagina respectively, and an expanded active position as featured in FIGS. 11b, 11d and 11f wherein the device provides pressure through the vaginal wall on the mid urethra thus eliminating involuntary urination.

The anchoring member (102) when in place, is positioned in the section of the vagina facing the cervix, and its purpose is to anchor the device inside the vagina in the proper position to eliminate its backward slippage further back into the vagina. The pressure providing member (101) is intended to provide pressure on the vaginal wall, and through the vaginal wall to provide pressure on the mid urethra. Depending on the amount of pressure applied, the pressure providing member (101) either completely blocks the urethra from passage of urine both for voluntary and involuntary urination, or partially blocks the urethra, only eliminating involuntary urination while enabling voluntary urination In accordance with the embodiment shown in the FIG. 11, both the pressure providing member (101) and the anchoring member (102) have the same design. However anchoring member (102) may be of any anchoring design (expanded or rigid) since its purpose is not to provide pressure on the urethra, but merely serves as an anchorage to position the device properly inside the vagina. FIG. 11a illustrates a device including a spacer in the form of a longitudinally extending flexible rod (103) to which pressure providing member (101) and anchoring member (102) are attached, a soft cover (104) enclosing both pressure providing member and anchoring member, and an applicator (105) wherein the device (100) is located at the head of the applicator. The applicator includes a plunger (106) for pushing the device into the vagina. When plunger (106) is pushed, the device (100) may assume its expanded position, as shown in FIG. 11b. A string (107) attached to the device, enables the user to pull the device out of the vagina at the end of usage. FIG. 11c illustrates a cross section of the pressure providing member (101), which in the present embodiment is identical to the anchoring member (102), although the anchoring member may assume different forms. The pressure providing member (101) and the anchoring member (102) are made up of two, three or four telescopically extendible arms (109), in the present figure there are three such arms. The member is composed of a base (108) having suitable holes therein in accordance with the number of telescopic arms projecting through the holes. The base (108) may be composed of a single element, or may be an assembly of more than one element. Each telescopic arm (109) is composed of an inner extendible coil (110) and a pressure applying surface (111) which comes into contact with the vaginal wall when the device is in the expanded position. Pressure applying surface (111) is preferably rounded so as to avoid vaginal pain when the device is present inside the vagina. The telescopic arms (109) may extend not by the expansion of a coil but rather by the expansion of a flexible material. In the collapsed position, rings (112, 113) of the telescopic arm (109) overlap each other due to the compression of the coil (110) within the member. FIG. 11d illustrates the telescopic arm (109) wherein the coil (110) is in the extended form, so that rings (112, 113) only partially overlap, and in that position the telescopic arm (109) element is telescopically extended. The member also contains a ring (114), which ensures that the telescopic arm (109) remains concentric within the base (108) and does not move laterally.

When inside the applicator (105) (FIG. 11a), the walls of the applicator apply force on pressure applying surfaces (111), thus placing the pressure providing member (101) in a collapsed position. A string (not shown) is attached to three coils by a suitable number of string-extensions (not shown) present in base (108), so that pulling of the string causes collapse of the coil (110), thus leading to collapse of the whole telescopic arm (109), to revert the member back to the closed position as shown in FIG. 11c, thus enabling removal of the device from the vagina.

FIGS. 12a-12f illustrate an embodiment of the invention identical to the one shown in FIGS. 11a-11f, so that each element in FIG. 12 is marked with the identical number of the element in FIG. 11 with a prime (') indication. The difference being that while FIG. 11 describes three telescopic arms (109) FIG. 12 describes four telescopic arms (109'). Since the distance between the arms (109') is smaller in the device (101') of FIG. 12 as compared to that of FIG. 11, at lease one pressure applying surface (111') rests directly beneath the mid-urethera providing direct pressure on the urethra. This ensure essentially complete blockage of urine passage through the urethra. This device is suitable for situations wherein the involuntary urination is more pronounces such as when the woman is undergoing heavy physical activity.

Figure 12A:
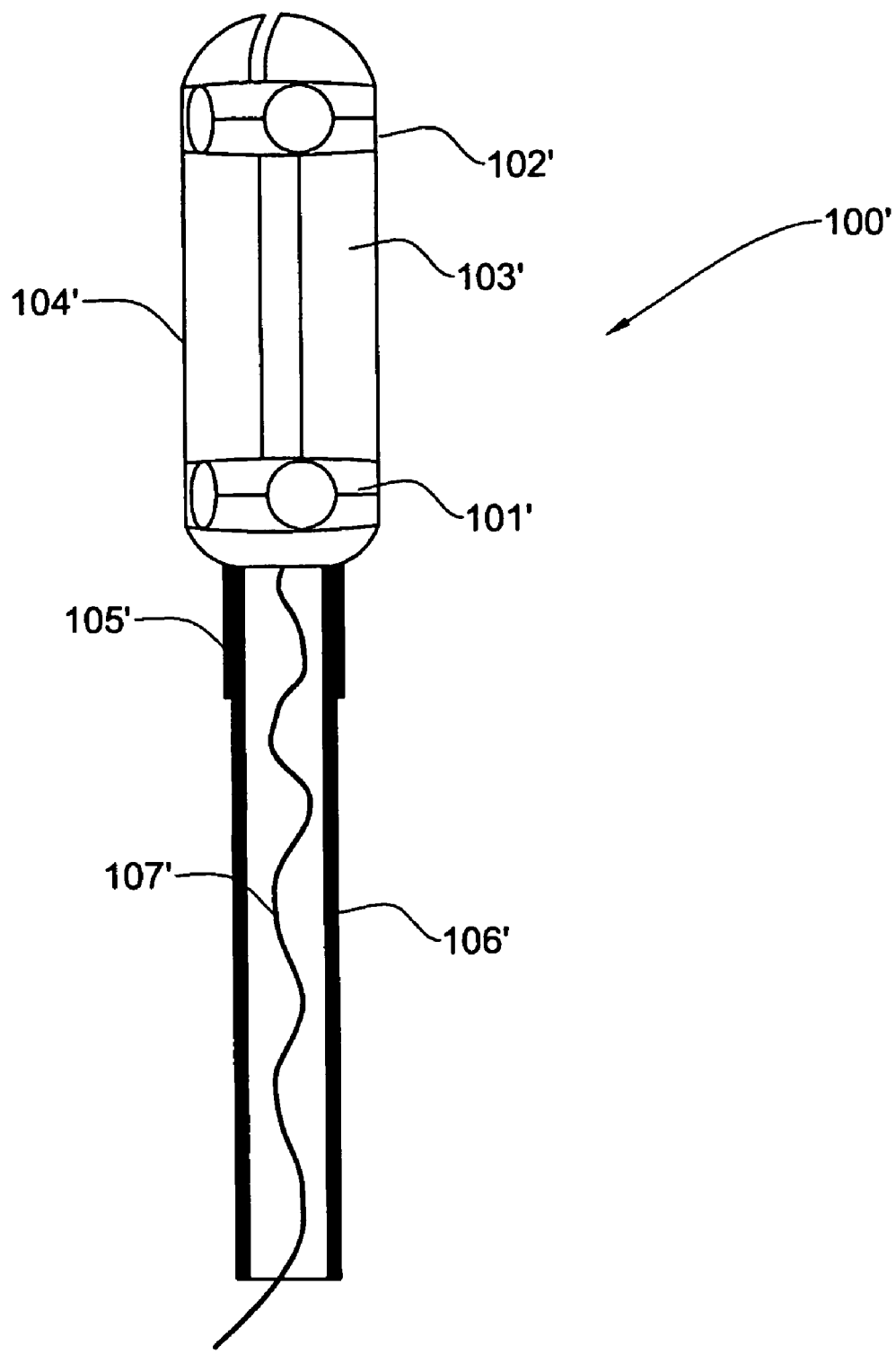
FIGS. 12a, 12b, 12c, 12d, 12e and 12f illustrate an embodiment of the device as shown in FIGS. 11a-11e having 4 arms.
Figure 12B:
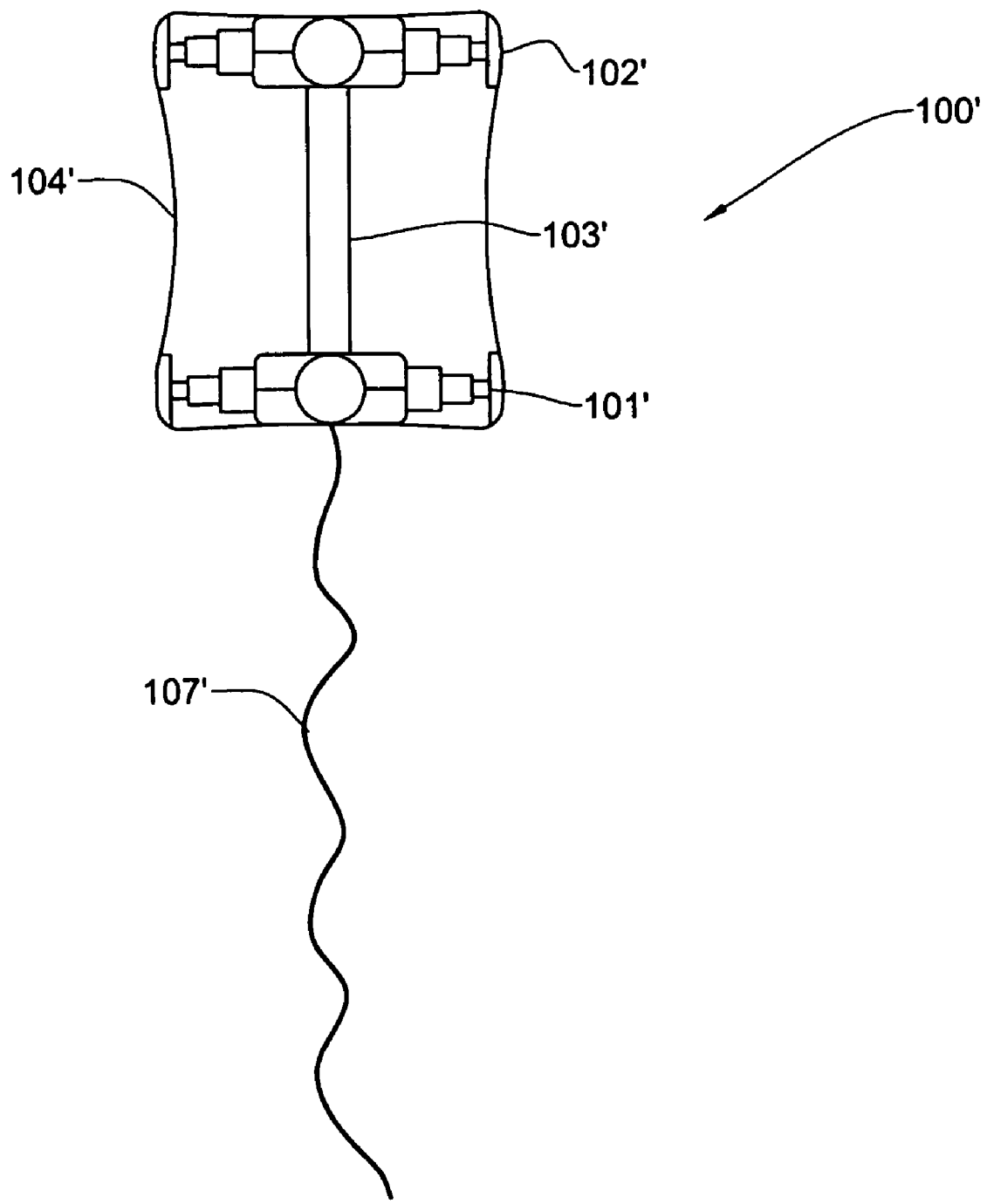
Figure 12C:
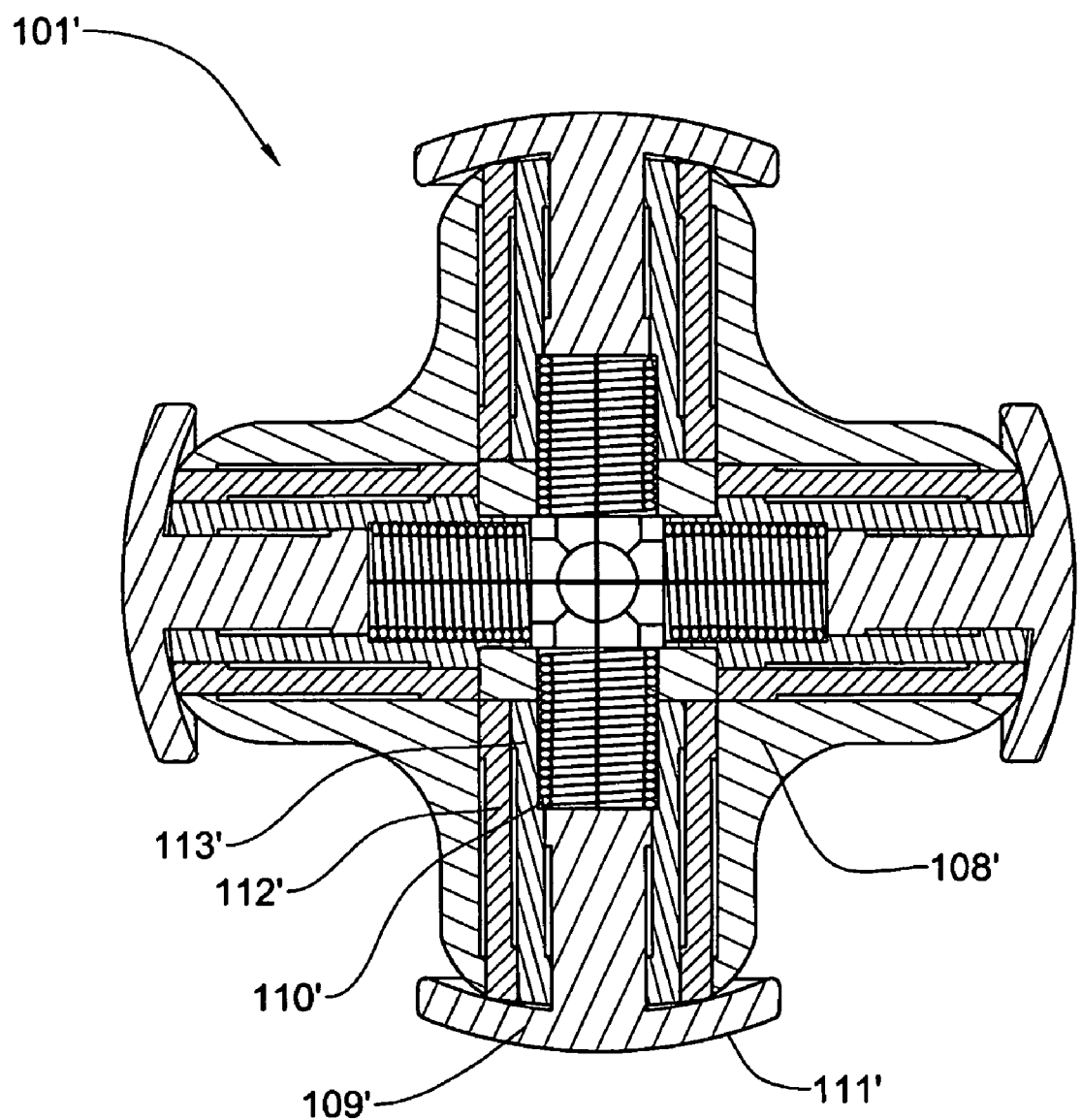
Figure 12D:
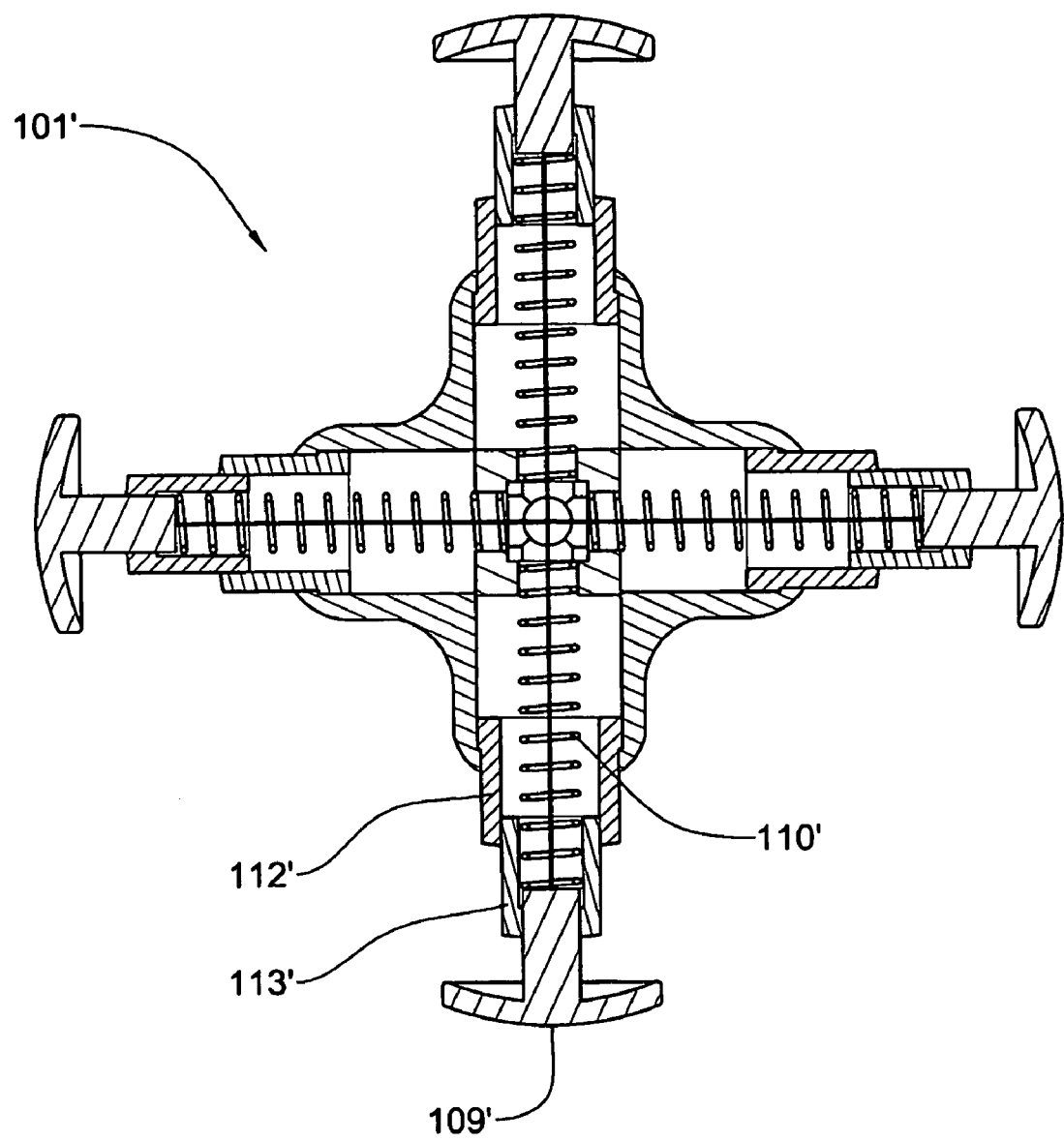
Figure 12E:
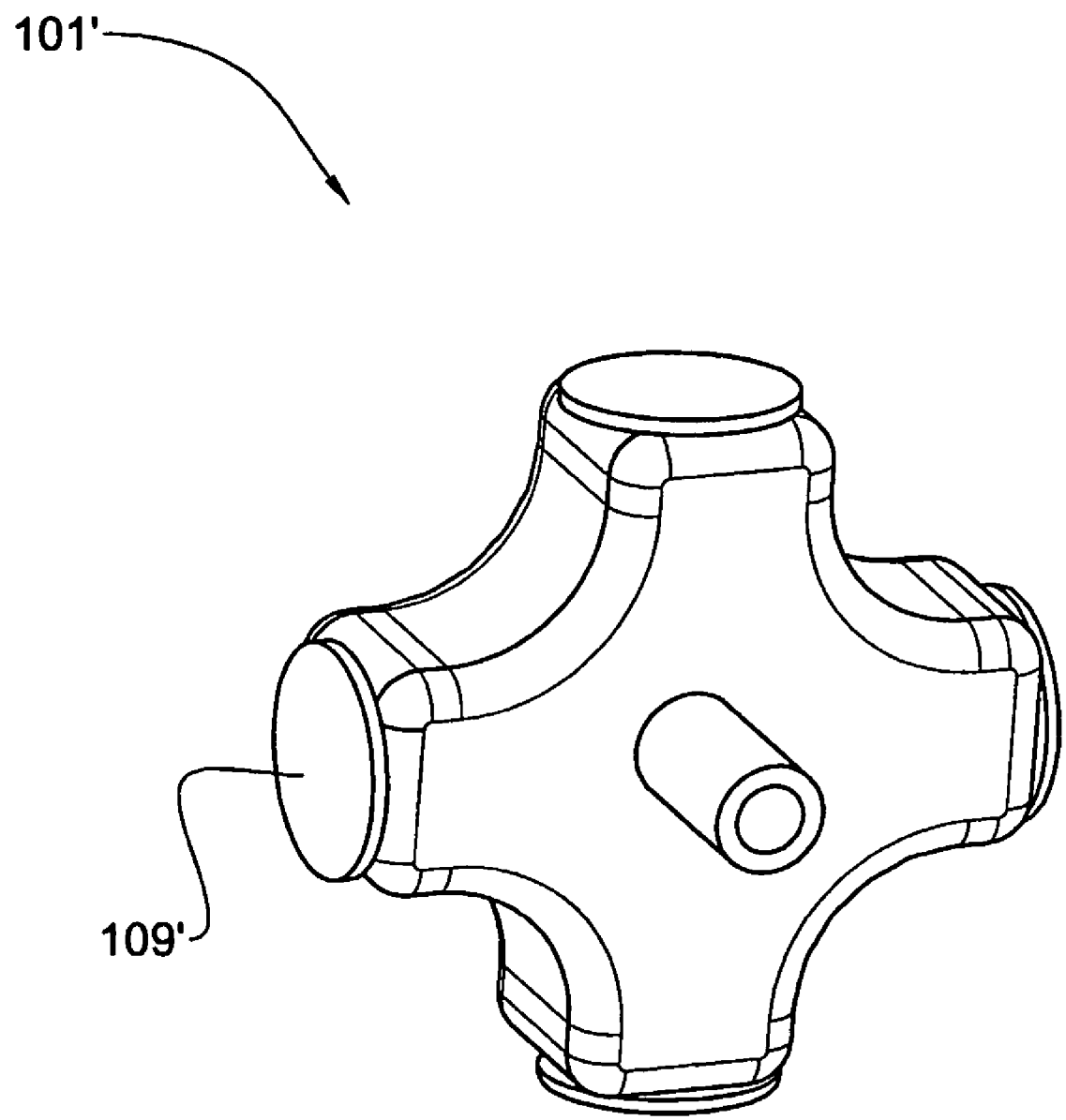
Figure 12F:
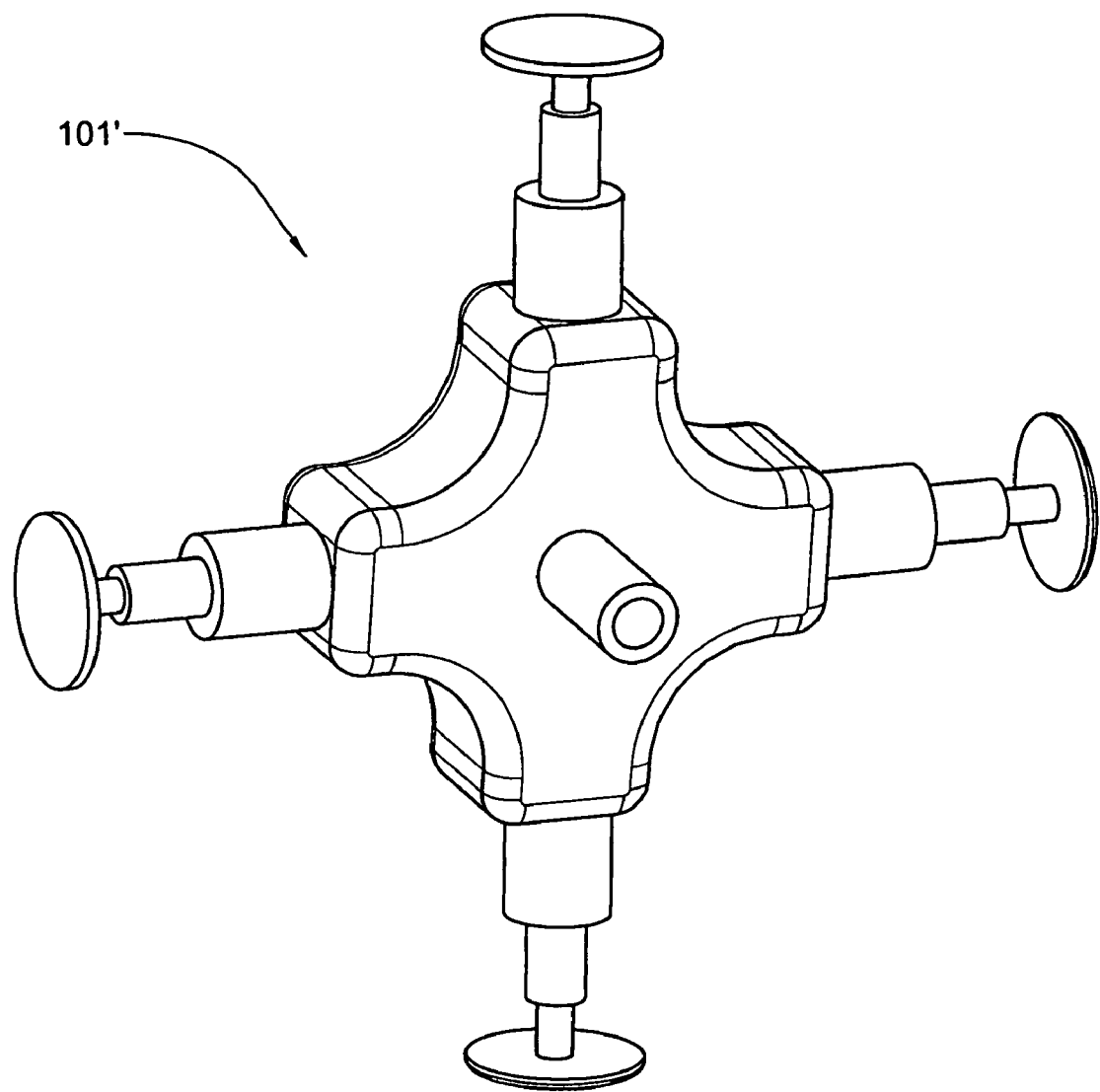

Reference is made to FIG. 13 which illustrates another embodiment of the device of the invention (120) comprising an anchoring member (121), a pressure providing member (122) and a soft cover (123). The anchoring member (121) and the pressure providing member (122) are connected thereinbetween by a flexible longitudinal rode (124). FIG. 13a illustrates the device (120) in a collapsed-inactive position for insertion and removal from the vagina, while FIG. 12b illustrates the device (120) in an expanded active position for providing pressure on the urethra.

Figure 13A:
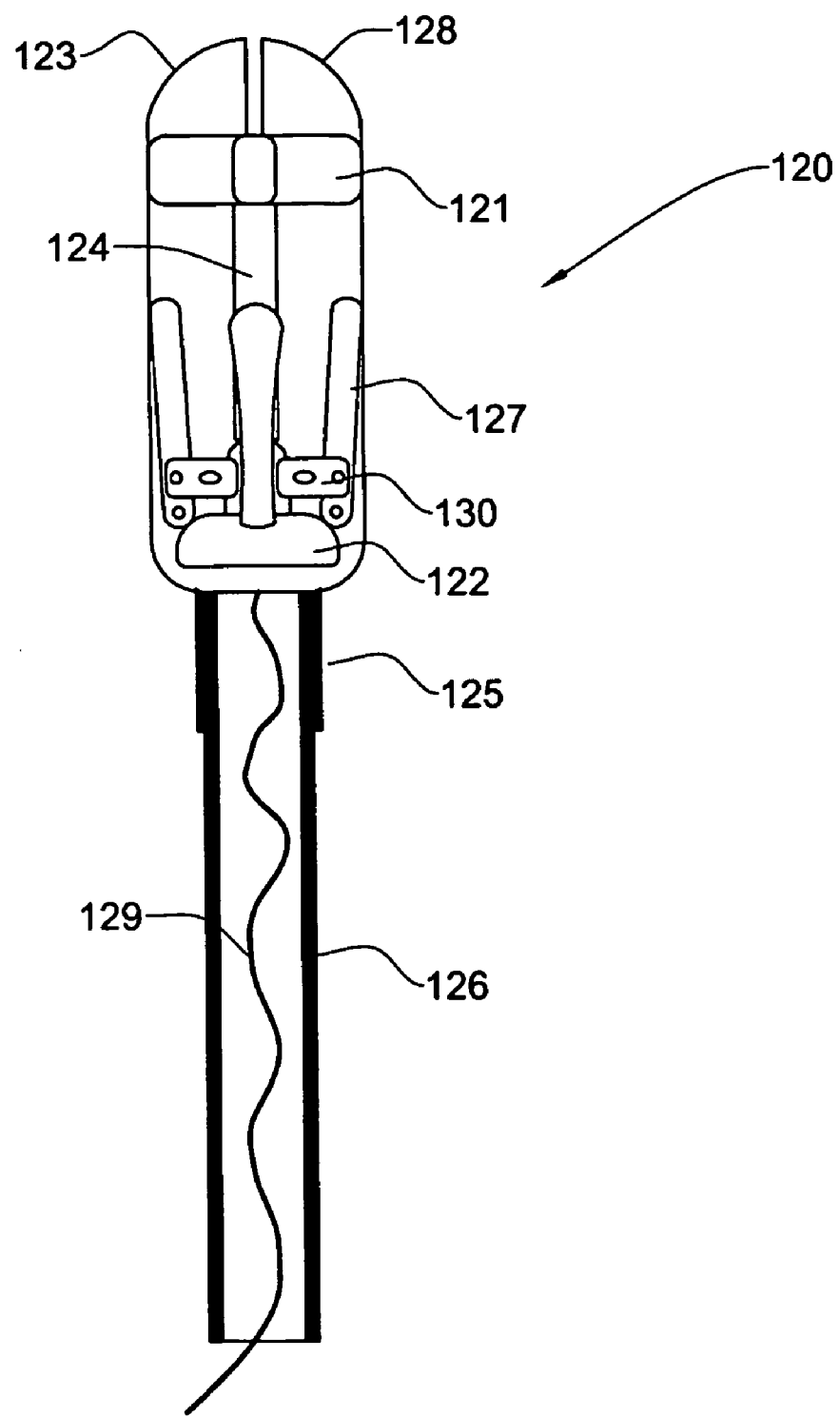
FIGS. 13a, 13b, 13c, 13d and 13e illustrate another embodiment of the device wherein the pressure providing member and the anchoring member have different design.
Figure 13B:
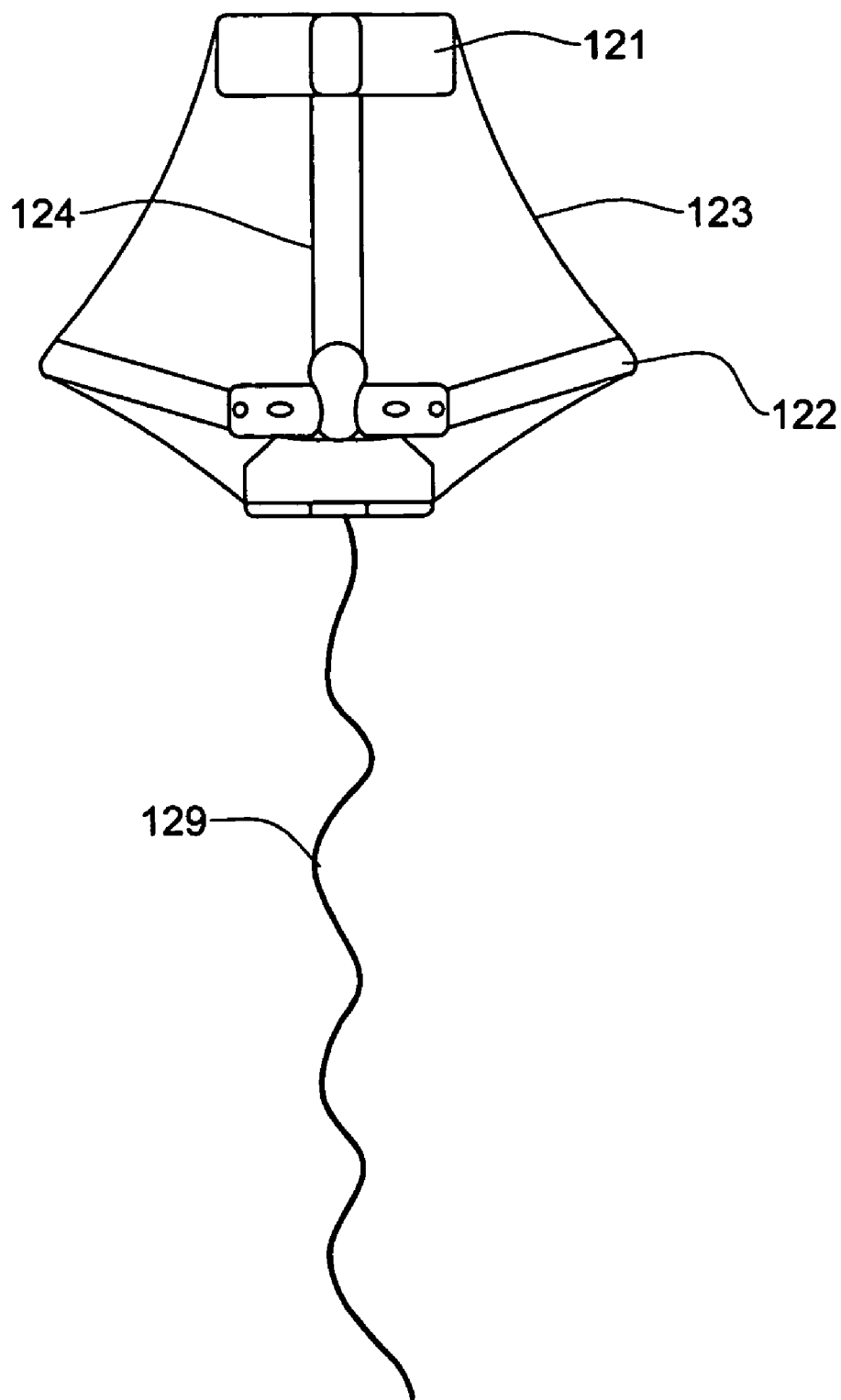
Figure 13C:
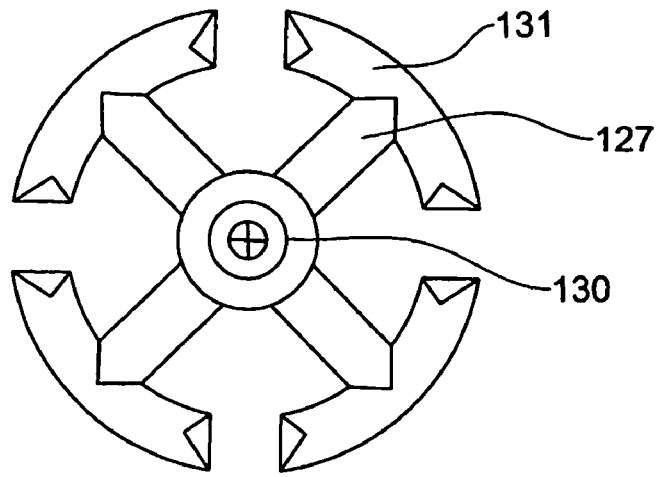
Figure 13D:
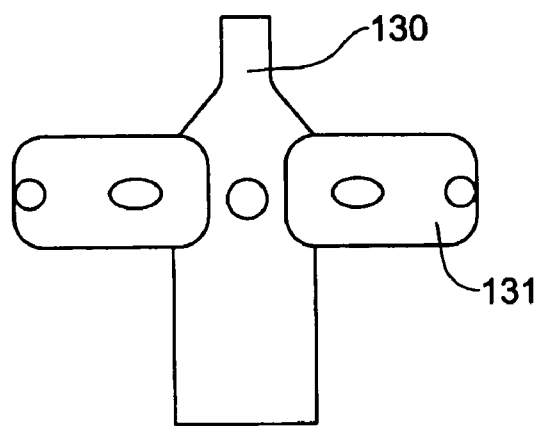
Figure 13E:
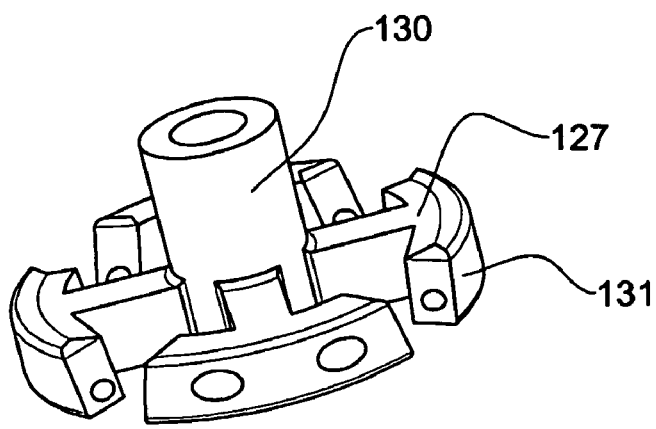

FIG. 13a illustrates the device (120) within an applicator (125). The applicator also contains a plunger (126). When the plunger (126) is pushed, the device (120) moves through the applicator (125), and the distal end (128) of the applicator opens to allow passage of the device therethrough. The device also comprises a string (129), which enables the removal of the device from the vagina by pull. The anchoring member (121) may be identical to any anchoring member of the previous embodiments, for example, the telescopic anchoring member as indicated in element (102) in FIG. 11a. The pressure providing member (122) is attached to the anchoring member (121) through a flexible rod (124). The expansion of the pressure providing member (122) is achieved by way of a screw mechanism shown in detail in FIGS. 13c-13e. Arms (127) each equipped with a pressure providing surface (131) provide together a cross-like construction having in the center a nut (130), which is loosely screwed on the base of the flexible rod (124) which has corresponding groves (not shown). Movement of the loose nut (130) towards the distal end of the device on the flexible rod (124) encloses arms (127) within the nut (130) causing them to fold in an umbrella-like fashion. Movement of the nut (130) in the other direction caused the arms (127) to expand laterally sideways providing pressure on the vagina walls. The pulling of string (129) causes the nut to move so as to collapse the arms again.

Figure 14A:
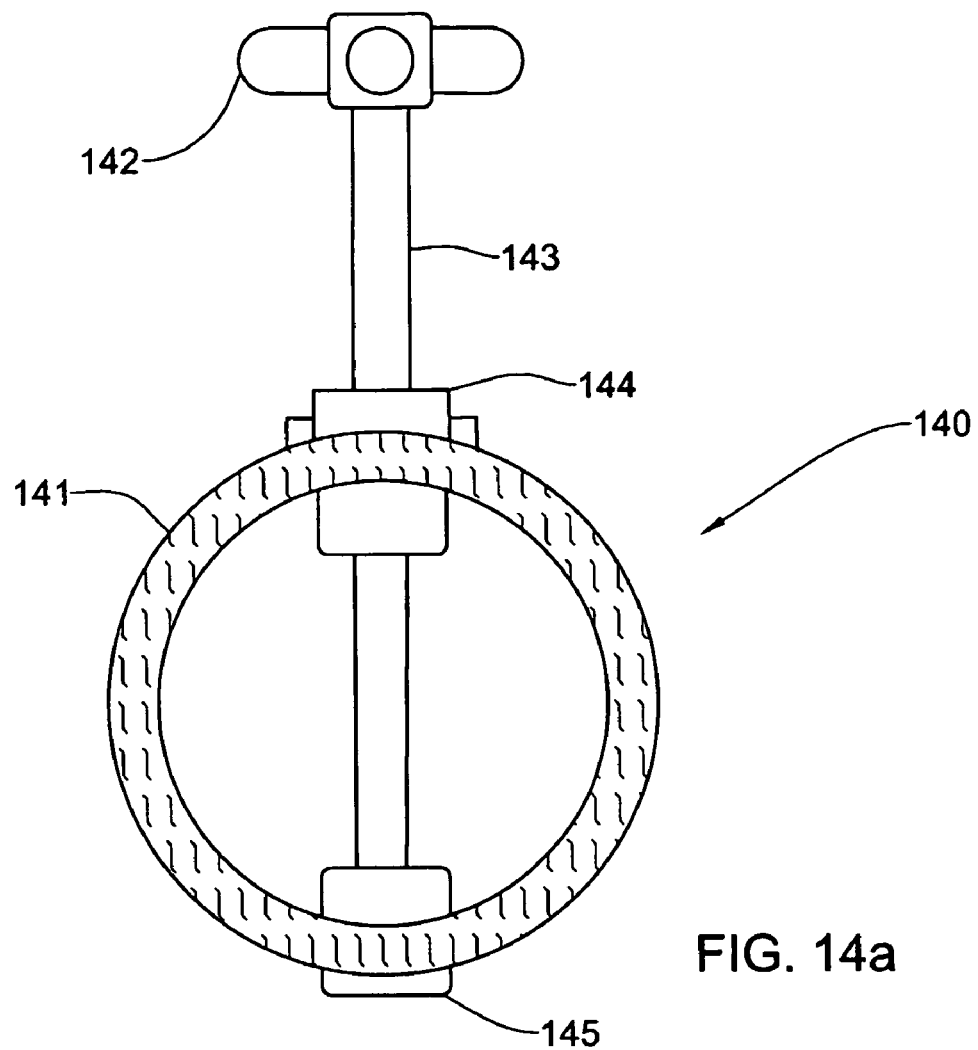
FIGS. 14a, 14b, 14c and 14d illustrate another embodiment of the device wherein the pressure providing member has a ring.
Figure 14B:
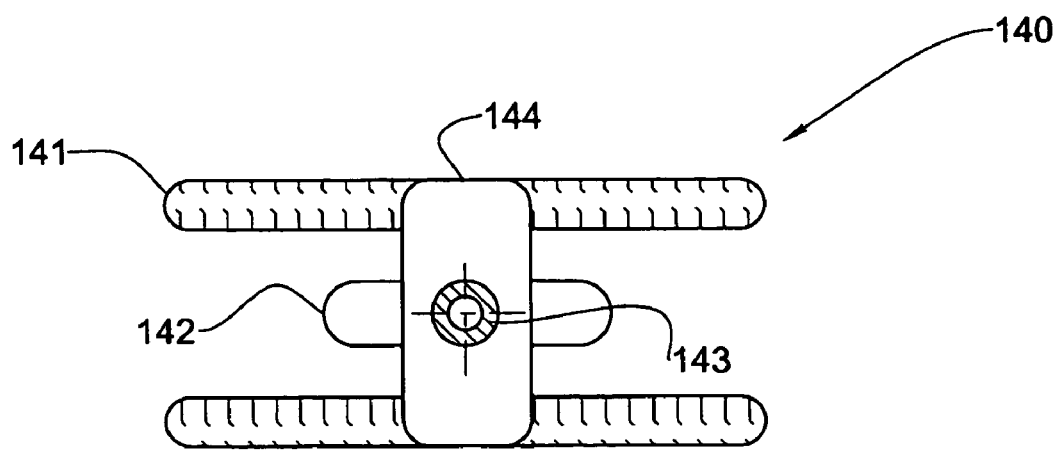
Figure 14C:
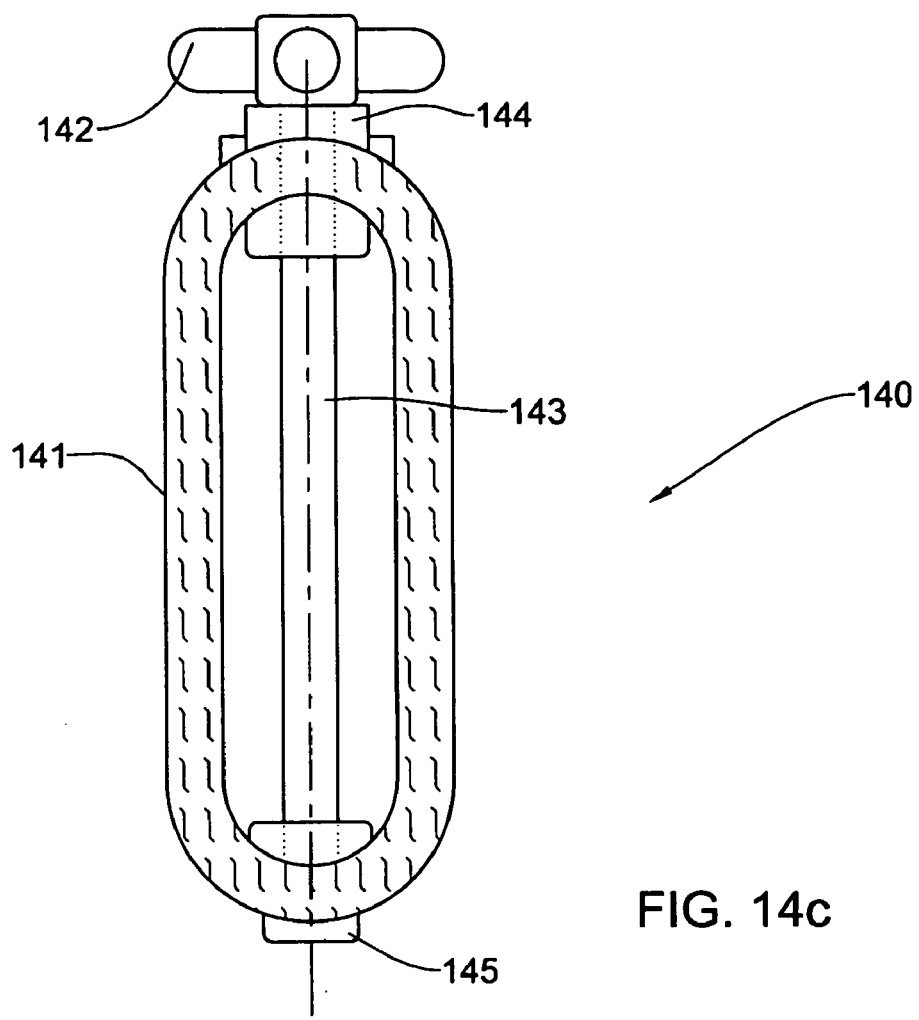
Figure 14D:
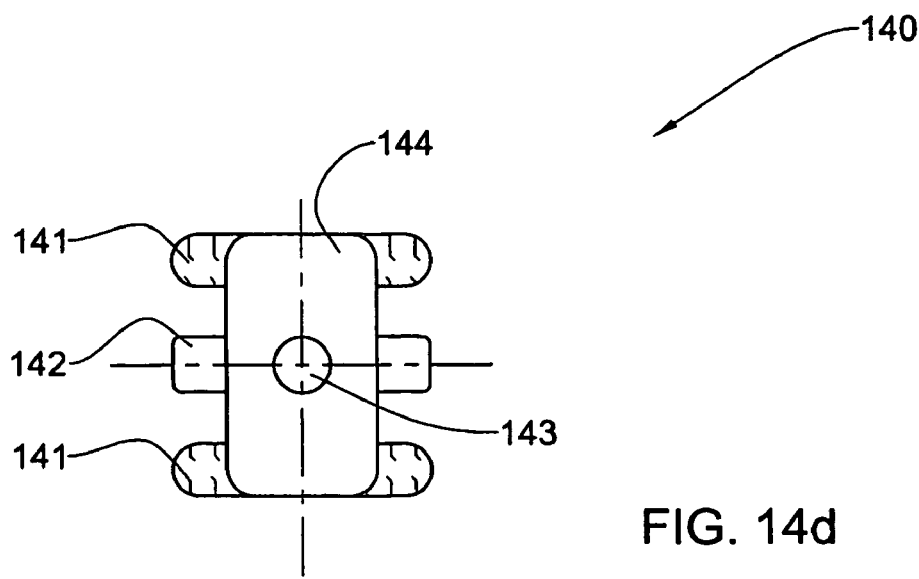

FIG. 14a illustrates a device (140) comprising a pressure providing member (141) and an anchoring member (142). The pressure providing member (141) is attached to the anchoring member (142) through a flexible rod (143). The pressure providing member (141) having a ring form is attached to the flexible rod (143) with an frontal mount (145) and an posterior mount (144). The pressure providing member (141) due to the flexible material from which it is made is capable of a transition between a collapsed, closed position as featured in FIG. 14c, where the pressure providing member (141) assumes an elliptical configuration, said collapsed position suitable for insertion and removal of the device into or from the vagina, and an expanded active position as featured in FIG. 14a, where the pressure providing member (141) assumes a circular configuration, wherein the device provides pressure through the vaginal wall on the mid urethra thus eliminating involuntary urination. The anchoring member (142) as shown in FIGS. 14a-14c is rigid, contrary to the anchoring member, as shown in the previous figures, which is capable of a transition between a collapsed position and expended position. FIGS. 14b and 14d illustrate the top view of the device (140) in expended position and collapsed position, respectively.

EXAMPLE 1

Figure 15:
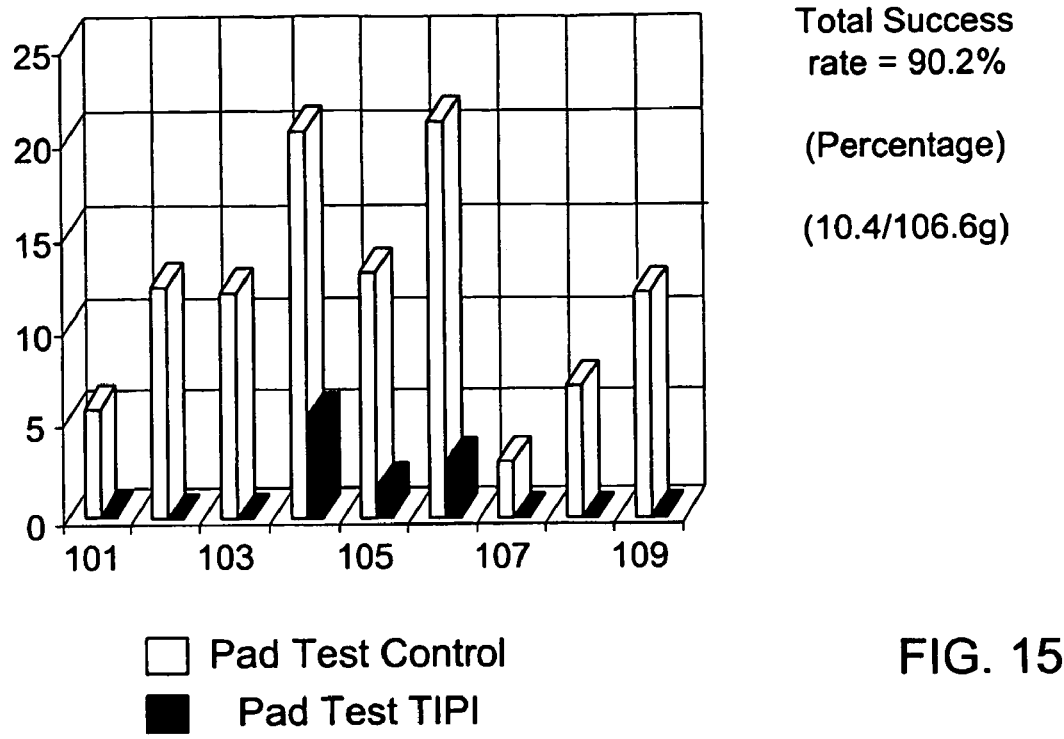
FIG. 15 shows the results of "pad test assay" in 9 non selected women tested for involuntary urination during 1 hour of physical exercised with (dark bars) and without (light bars) the device of the invention.
Figure 16:
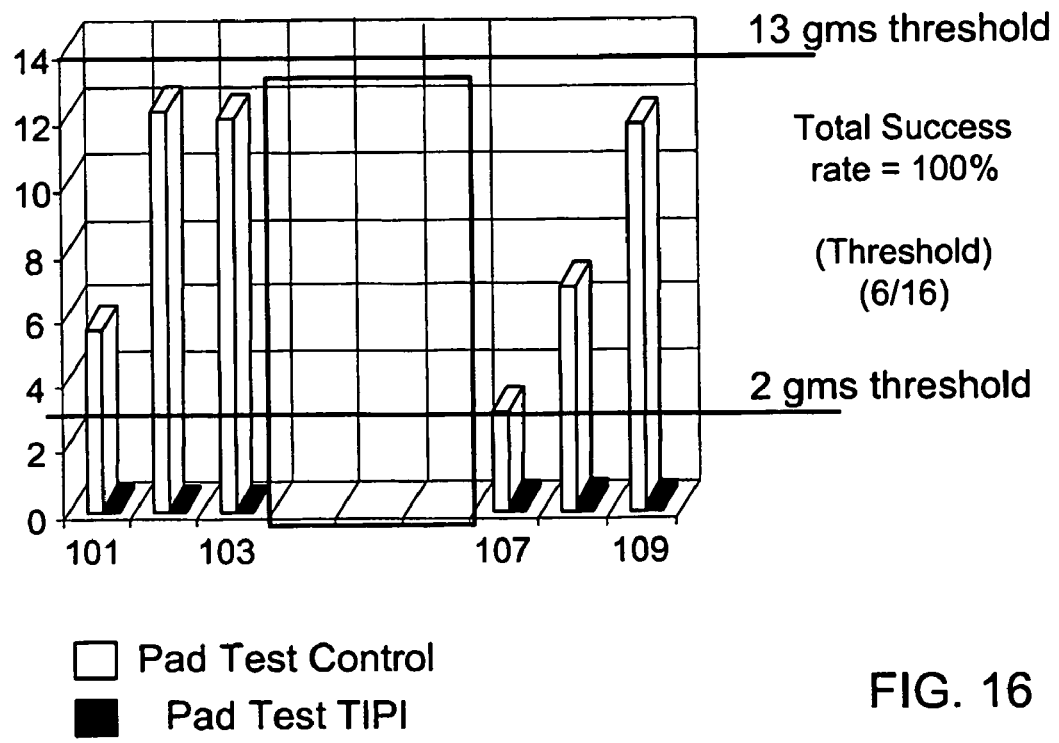
FIG. 16 shows another result of the "pad test assay" in 6 selected women tested for involuntary urination during 1 hour of physical activity with (dark bars) and without (light bars) the device of the invention.
Figure 17:
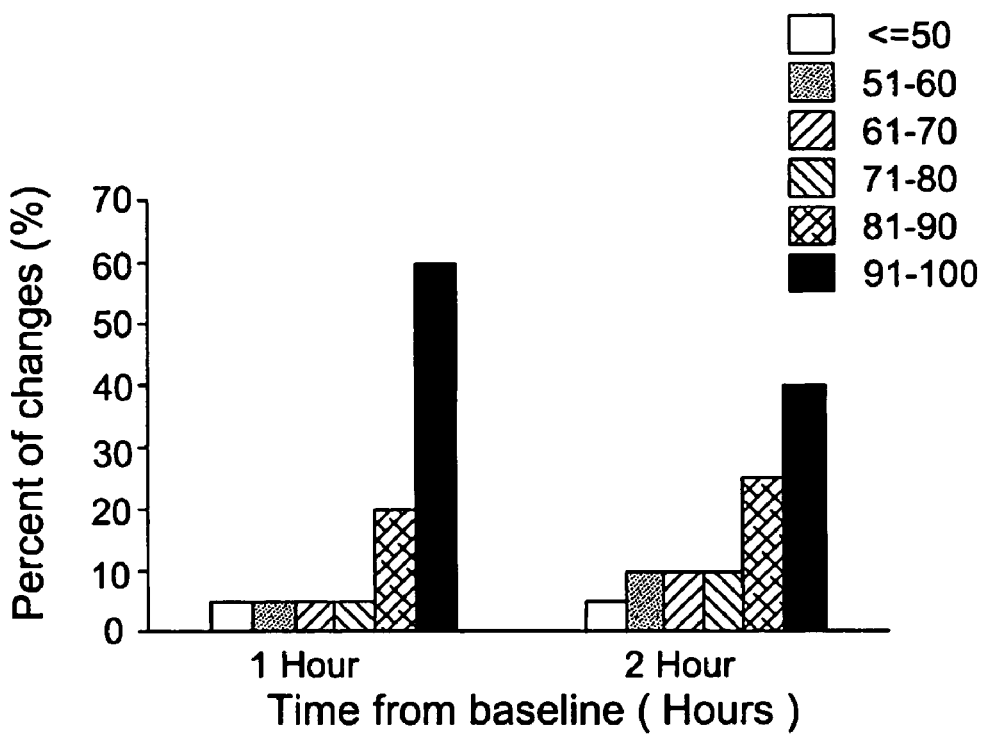
FIG. 17 shows frequency of patients responding to treatment with the device by level of changes 1 and 6 hours from control period (Groups 1 & 3)
Figure 18:
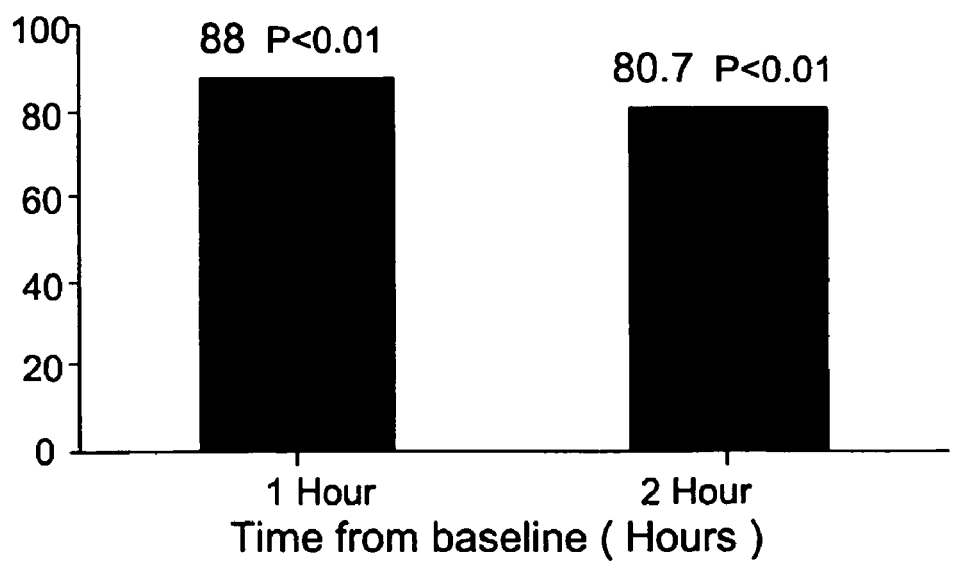
FIG. 18 shows mean weight changes in pad assay (groups 1 and 3)

Elimination of Involuntary Urination by Use of the Device of the Invention 9 women suffering from involuntary urination were chosen for the purpose of the experiment. Prior to the use of the device of the invention, the women chosen underwent a "pad test", wherein a dry pad was placed in their panties for a period of 60 minutes, and during that time, all 9 women performed identical and predefined physical activity. At the end of 60 minutes, the pad was weighted and the addition of weight due to moisture (including vaginal discharges, sweat and urination) was noted. The day after, the same experiment (i.e. weight of a pad before and after 60 minutes of predefined physical exercise) was conducted again, but at this stage with the device of the invention as specified in FIGS. 5 and 6 inserted into the vagina of the women. The results are shown in FIG. 14 for the difference between the weighted pad after one hour of physical exercise, and in FIG. 15 for the same results after defining the correct thresholds (in this case— mild incontinence=<2 gms+<13 gms.

As can be seen in both figures, in all tested subjects, the device of the invention caused substantial decrease in the amount of moisture present in the pad as compared to the result obtained in the same women on the previous day, without the device of the invention.

EXAMPLE 2

Comparative Study on Three Different Devices of the Invention

A total of 30 patients were screened and entered to the study, 10 on each study group. One patient from group II was excluded (Dropout) after reporting on inconvenience and dissatisfaction in using the device of the invention.

The final study population included 29 women divided into 3 study groups; each used a different type of device of the invention. In all 3 groups the women used the device and in the control period they weren't using any device.

The pads were weighted after 1-hour stress period (one hour pad test) and again at 6 hours, after another 5 hours of daily routine. The difference in the measured weights between the device period and the control period was calculated and presented as an absolute change and as a relative change (%) from the DEVICE period. The differences are presented for each study group and for each time point. The results show lower measured weight in the device wearing period than in the control period for all 3 groups on each measurement. The differences were found statistically significant in all 3 study groups after 1 and 6 hours. The above results are presented in tables 1.1, 1.2, 2.1, 2.2.

On stage 2 of the statistical analysis, group II, which showed improvement but not as good as groups I and III was excluded from the analyses and groups I and III, which were very similar in design and showed similar results, were combined into one group. The difference in the measured weight between the device period and control period was found statistically significant after 1 and 6 hours, for the absolute measured changes as well as for the relative changes calculated in percents. The above results are presented in tables 3.1, 3.2, 4.1, 4.2).

Statistical Methods

The following statistical tests were used in the analysis of the data presented in this study:

The Paired T-test and Non-parametric Sign Rank Test were applied for testing differences between the Device period v.s. Control period for weight changes of pad.

All tests applied were two-tailed, and p value of 5% or less was considered statistically significant. The data was analyzed using the SAS software (SAS Institute, Cary N.C.).

References: SAS Procedures Guide, SAS Institute Inc.
SAS/STAT User's Guide, SAS Institute Inc.

TABLE 1.1

Mean Weight of Pad (After 1 Hour), by group N, Mean, Median, Stderr, Minimum & Maximum values

| Group | | N | Mean | Median | StdErr | Min | Max |
|---|---|---|---|---|---|---|---|
| 1 | Control | 10 | 11.59 | 11.95 | 1.86 | 3.10 | 21.20 |
|   | Device | 10 | 1.68 | 0.15 | 0.77 | 0.00 | 6.50 |
| 2 | Control | 9 | 11.66 | 9.70 | 3.33 | 2.50 | 35.00 |
|   | Device | 9 | 5.63 | 2.70 | 2.90 | 0.00 | 26.40 |
| 3 | Control | 10 | 12.36 | 7.25 | 4.89 | 3.30 | 53.80 |
|   | Device | 10 | 0.55 | 0.10 | 0.31 | 0.00 | 3.10 |

The table presents the mean measured weight of the pads for the Device period and for the control period for each study group after 1 hour of using. The mean weight was found statistically significant lower in the Device control in all 3 groups. However, the results show similar and great change in groups 1 and 3, and smaller change in group 2

TABLE 1.2

Mean of Weight Changes from Control (After 1 Hour), by group N, Mean, Median, Stderr & P-Value

| Group | | N | Mean | Median | StdErr | P-Value |
|---|---|---|---|---|---|---|
| 1 | Changes from Control | 10 | 9.91 | 11.70 | 1.65 | <.001 |
|   | Changes (%) from Control | 10 | 86.86 | 96.96 | 7.00 | <.001 |
| 2 | Changes from Control | 9 | 6.02 | 6.60 | 1.49 | 0.004 |
|   | Changes (%) from Control | 9 | 63.90 | 76.92 | 13.23 | 0.001 |
| 3 | Changes from Control | 10 | 11.81 | 6.00 | 4.99 | 0.042 |
|   | Changes (%) from Control | 10 | 88.67 | 98.92 | 5.34 | <.001 |

The table presents the absolute and relative (%) change in the Device period from the control period for each study group after 1 hour of using. The changes were found statistically significant in all 3 groups in the absolute change as well as in the relative change.

TABLE 2.1

Mean Weight of Pad (After 6 Hours), by group N, Mean, Median, Stderr, Minimum & Maximum values

| Group | | N | Mean | Median | StdErr | Min | Max |
|---|---|---|---|---|---|---|---|
| 1 | Control | 10 | 13.21 | 12.85 | 2.27 | 3.50 | 28.40 |
|   | Device | 10 | 2.48 | 1.95 | 0.66 | 0.60 | 6.80 |

TABLE 2.1-continued

Mean Weight of Pad (After 6 Hours), by group N,
Mean, Median, Stderr, Minimum & Maximum values

| Group | | N | Mean | Median | StdErr | Min | Max |
|---|---|---|---|---|---|---|---|
| 2 | Control | 9 | 14.24 | 9.90 | 3.98 | 2.60 | 35.20 |
|   | Device | 9 | 7.78 | 3.20 | 3.33 | 0.00 | 29.30 |
| 3 | Control | 10 | 14.37 | 10.50 | 4.82 | 4.10 | 54.80 |
|   | Device | 10 | 1.48 | 1.30 | 0.38 | 0.00 | 4.40 |

The table presents the mean measured weight of the pads for the Device period and for the control period for each study group after 6 hours of using. The mean weight was found statistically significant lower in the Device control in all 3 groups. However, the results show similar and great change in groups 1 and 3, and smaller change in group 2.

TABLE 2.2

Mean of Weight Changes from Control (After 6 Hours),
by group N, Mean, Median, Stderr & P-Value

| Group | | N | Mean | Median | StdErr | P-Value |
|---|---|---|---|---|---|---|
| 1 | Changes from Control | 10 | 10.73 | 11.30 | 2.09 | <.001 |
|   | Changes (%) from Control | 10 | 79.98 | 86.17 | 5.71 | <.001 |
| 2 | Changes from Control | 9 | 6.47 | 5.90 | 2.84 | 0.053 |
|   | Changes (%) from Control | 9 | 51.45 | 73.31 | 17.02 | 0.017 |
| 3 | Changes from Control | 10 | 12.89 | 9.50 | 4.83 | 0.026 |
|   | Changes (%) from Control | 10 | 81.50 | 90.82 | 5.57 | <.001 |

The table presents the absolute and relative (%) change in the Device period from the control period for each study group after 6 hours of using. The changes were found statistically significant in all 3 groups in the absolute change as well as in the relative change.

TABLE 3.1

Mean of Weight Changes from Control (After 1 Hours) Groups 1, 3
N, Mean, Median, Stderr & P-Value

| | N | Mean | Median | StdErr | P-Value |
|---|---|---|---|---|---|
| Changes from Control | 20 | 10.86 | 8.55 | 2.57 | <.001 |
| Changes (%) from Control | 20 | 87.77 | 97.50 | 4.29 | <.001 |

The table presents the absolute and relative (%) change in the Device period from the control period for the combined group including groups 1 and 3, after 1 hour of using. The change's effect was found statistically significant

TABLE 3.2

Mean of Weight Changes from Control (After 6 Hours) Groups 1, 3
N, Mean, Median, Stderr & P-Value

| | N | Mean | Median | StdErr | P-Value |
|---|---|---|---|---|---|
| Changes from Control | 20 | 11.81 | 10.15 | 2.57 | <.001 |
| Changes (%) from Control | 20 | 80.74 | 87.79 | 3.89 | <.001 |

The table presents the absolute and relative (%) change in the Device period from the control period for the combined group including groups 1 and 3, after 6 hours of using. The results on this time point are similar to the results after 1 hour of using. The absolute and the relative changes were found statistically significant.

TABLE 4.1

Frequency (N, %) of patients by levels of Change
after 1 hour, Groups 1, 3

| Percent of changes | N | % |
|---|---|---|
| <=50 | 1 | 5.00 |
| 51-60 | 1 | 5.00 |
| 61-70 | 1 | 5.00 |
| 71-80 | 1 | 5.00 |
| 81-90 | 4 | 20.00 |
| 91-100 | 12 | 60.00 |
| Total | 20 | 100.00 |

The table presents the relative change (%) from the control period for groups 1 and 3 together after 1 hour of using. The relative change is presented in categories: less than 50% change, 51-60%, 61-70%, 71-80%, 81-90% and 91-100%. The results show that 80% of the women had more than 80% change, and 60% of the women had over 90% change.

TABLE 4.2

Frequency (N, %) of patients by levels of Change
after 6 hours, Groups 1, 3

| Percent of changes | N | % |
|---|---|---|
| <=50 | 1 | 5.00 |
| 51-60 | 2 | 10.00 |
| 61-70 | 2 | 10.00 |
| 71-80 | 2 | 10.00 |
| 81-90 | 5 | 25.00 |
| 91-100 | 8 | 40.00 |
| Total | 20 | 100.00 |

The table presents the relative change (%) from the control period for groups 1 and 3 together after 6 hours of using. The relative change is presented in categories: less than 50% change, 51-60%, 61-70%, 71-80%, 81-90% and 91-100%. The results show that 65% of the women had more than 80% change, and 40% of the women had over 90% change.

TABLE 5.1

Frequency (N, %) of patients by categorical change
(<=2 grams, >2 grams), Groups 1, 3

| 2 gr | N | % |
|---|---|---|
| <=2 gr | 4 | 20.00 |
| >2 gr | 16 | 80.00 |
| Total | 20 | 100.00 |

The table presents the absolute change from control for groups 1 and 3 together, in 2 categories: 2 grams change or less and more than 2 grams change. The results show that 80% of the women had change of more than 2 grams.

The invention claimed is:
1. An apparatus for treating urinary incontinence, comprising:
a body; and,
a support member configured with a cradle support adapted for receipt of a urethra such that when said apparatus is lodged in a vagina said support member does not apply direct pressure to the urethra located within said vagina.

2. An apparatus in accordance with claim 1 wherein said support member is provided with at least two arms adapted to lie on either side of said urethra defining the cradle support therebetween.

3. An apparatus in accordance with claim 2 further comprising an anchoring member.

4. An apparatus in accordance with claim 2 wherein said arms are flexible.

5. An apparatus in accordance with claim 1 further comprising a cover, said cover covering at least said support member.

6. An apparatus in accordance with claim 1 further comprising a removal string.

7. An apparatus in accordance with claim 1 further comprising an applicator, said applicator adapted to insert at least said support member into a vagina.

8. An apparatus in accordance with claim 1 wherein said support member provides support at a mid-urethral region within said vagina.

9. An apparatus in accordance with claim 3 wherein said anchoring member is capable of a transition between a first collapsed position and a second expanded position.

10. An apparatus in accordance with claim 3 wherein said anchoring member is rigid.

11. An apparatus in accordance with claim 3 wherein said anchoring member is flexible.

12. An apparatus in accordance with claim 3 wherein said support member and said anchoring member are separate, connected to each other through a spacer.

13. An apparatus in accordance with claim 12 wherein said spacer is a flexible rod.

14. An apparatus in accordance with claim 3 wherein said anchoring member is provided with at least two arms.

15. An apparatus in accordance with claim 3 wherein when said apparatus is inserted in said vagina, said anchoring member is located between said support member and a uterine cervix located proximal to said vagina.

16. An apparatus in accordance with claim 1 wherein said support member is transitioned between a first collapsed position and a second expanded position through pneumatic means.

17. An apparatus in accordance with claim 1 wherein said support member is transitioned between a first collapsed position and a second expanded position by at least one balloon adapted for being inflated upon insertion of said apparatus into said vagina, and said support member is transitioned between said second expanded and said first collapsed positions for removal of said apparatus from the vagina by deflating said balloon.

18. An apparatus in accordance with claim 17 further comprising a one-way flexible valve mechanism for enabling inflation and deflation of said balloon.

19. An apparatus according to claim 15 wherein said anchoring member is comprised of at least one balloon adapted for being inflated upon insertion of said apparatus into said vagina thereby anchoring the apparatus in said vagina and preventing posterior movement of said apparatus in said vagina.

20. An apparatus in accordance with claim 17 wherein at least one balloon is substantially circular-shaped.

21. An apparatus in accordance with claim 17 comprising a first and second balloon, the second balloon having a diameter that is larger than the diameter of said first balloon.

22. An apparatus in accordance with claim 17 comprising a first and second balloon, the first balloon and the second balloon further comprising at least one opening extending there through.

23. An apparatus in accordance with claim 1 wherein said support member functions through pneumatic-mechanical means.

24. A device in accordance with claim 23, wherein the support member comprises at least one balloon coupled to at least two support arms such that transition of the member from a first collapsed position to a second expanded position is by inflating the balloon so that the arms assume an extended configuration.

25. An apparatus in accordance with claim 24, comprising one balloon having four support arms coupled thereto.

26. An apparatus in accordance with claim 24, wherein the support member comprises a balloon, and wherein the balloon is coupled to two expanded support arms.

27. An apparatus in accordance with claim 1, wherein said support member is provided with at least one star-shaped element having at least three prongs.

28. An apparatus in accordance with claim 27, wherein said body is comprised of a flexible material.

29. An apparatus in accordance with claim 3, wherein said anchoring member is provided with at least one star-shape element.

30. An apparatus in accordance with claim 29, wherein each star-shaped element comprises four prongs.

31. An apparatus in accordance with claim 29, wherein at least one prong of the star-shaped element comprises an inflatable balloon located at the end thereof.

32. An apparatus in accordance with claim 31, wherein each prong has an inflatable balloon located at the end thereof.

33. An apparatus in accordance with claim 31, wherein the star-shaped elements and said body comprise an inflation passageway for enabling inflation of said inflatable balloons.

34. An apparatus in accordance with claim 27, wherein the star-shaped elements are comprised of a flexible material such that when in a first collapsed position, said star-shaped elements assume a compressed state and when in a second expanded position, said star-shaped elements assume an expanded state.

35. An apparatus in accordance with claim 34, wherein said star-shaped elements comprise four openings through which extending arms may pass following insertion of the device into the vagina.

36. An apparatus in accordance with claim 1, wherein the support member comprises at least two telescopically extendible arms and wherein a transition from a first position to a second position is by the expanding of said telescopic arms, and wherein said transition from said second position to said first position is by the compression of said telescopic arms.

37. An apparatus in accordance with claim 36, wherein said expansion of the telescopic arms is by means of a coil.

38. An apparatus in accordance with claim 36, wherein said expansion of the telescopic arms is by means of a flexible material.

39. An apparatus in accordance with claim 1, wherein the pressure providing member is composed of 2 to 4 arms connected to a longitudinal rod, the member further comprising a nut capable of a screw mechanism on the rods in one direction, the arms transition to the collapse position parallel with the rod, and when the nut moves in the other direction, the arms transition to an expanded position providing pressure on the vaginal wall.

40. An apparatus in accordance with claim 3, wherein the anchoring member is identical in construction to the support member.

41. An apparatus in accordance with claim 3, comprising two anchoring members, when the device is positioned within the vagina, both anchoring elements being posterior to the pressure providing member.

42. An apparatus in accordance with claim 3, wherein the anchoring member is of different design from the support member.

43. A system for inserting an apparatus for treating urinary incontinence, comprising:
 a body of the apparatus for treating urinary incontinence;
 a support member configured with a cradle support adapted for receipt of a urethra such that when said apparatus is lodged in a vagina said support member does not apply direct pressure to a urethra located within said vagina; and,
 an applicator coupled to said apparatus for facilitating insertion of the apparatus into the vagina.

44. A system in accordance with claim 43 wherein said applicator maintains the support member and an anchoring member in a first collapsed position, while removal of the device from the applicator transitions the device members from said collapsed position to a second expanded position.

45. A system according to claim 44 wherein said applicator further comprises a plunger.

46. A method of using an apparatus for treating urinary incontinence, comprising:
 inserting said apparatus into a vagina;
 placing said apparatus in said vagina wherein a cradle support located on a support member of said apparatus receives a urethra such that the apparatus does not apply direct pressure to a urethra located within said vagina except during a stress incontinence event; and,
 removing said apparatus when done using.

47. An apparatus in accordance with claim 1 wherein said body is short.

48. An apparatus in accordance with claim 1 wherein said body is only a small portion of the overall apparatus length.

49. An apparatus in accordance with claim 1 wherein said support member is provided with a structure adapted to receive said urethra.

50. An apparatus in accordance with claim 49 wherein said structure is located at a mid-urethra position.

51. An apparatus in accordance with claim 8 wherein said support is provided only on a small portion of said mid-urethral region.

52. An apparatus in accordance with claim 29, wherein said at least one star-shaped element is comprised of a flexible material such that when in a first collapsed position, said star-shaped element assumes a compressed state and when in a second expanded position, said star-shaped element assumes an expanded state.

53. An apparatus in accordance with claim 1, wherein the support member is configured with a plurality of cradle supports.

54. An apparatus according to claim 1, wherein the cradle support is sized and positioned to lie beneath the pelvic floor, such that an increase in intra-abdominal pressure during a high stress event forces the urethra below the pelvic floor and into the cradle.

55. A method of claim 46, wherein a stress incontinence event is one that forces the urethra below the pelvic floor.

* * * * *